United States Patent
Etrych et al.

(10) Patent No.: US 9,173,949 B2
(45) Date of Patent: Nov. 3, 2015

(54) DENDRITIC HIGH-MOLECULAR-WEIGHT POLYMER DRUG CARRIERS AND THEIR CONJUGATES WITH DRUGS ESPECIALLY FOR TREATMENT OF SOLID TUMOURS

(75) Inventors: Tomas Etrych, Klinec (CZ); Petr Chytil, Kladno (CZ); Jiri Strohalm, Prague (CZ); Karel Ulbrich, Prague (CZ); Blanka Rihova, Prague (CZ)

(73) Assignees: USTAV MAKROMOLEKULARNI CHEMIE AV CR, V.V.I., Prague (CZ); MIKROBIOLOGICKY USTAV AV CR, V.V.I., Prague (CZ)

( * ) Notice: Subject to any disclaimer, the term of this patent is extended or adjusted under 35 U.S.C. 154(b) by 771 days.

(21) Appl. No.: 13/516,607

(22) PCT Filed: Dec. 14, 2010

(86) PCT No.: PCT/CZ2010/000131
§ 371 (c)(1),
(2), (4) Date: Jun. 15, 2012

(87) PCT Pub. No.: WO2011/072627
PCT Pub. Date: Jun. 23, 2011

(65) Prior Publication Data
US 2012/0296048 A1 Nov. 22, 2012

(30) Foreign Application Priority Data
Dec. 15, 2009 (CZ) .................................... 2009-844

(51) Int. Cl.
*C08F 20/56* (2006.01)
*A61K 47/48* (2006.01)
*C08G 83/00* (2006.01)

(52) U.S. Cl.
CPC ......... *A61K 47/482* (2013.01); *A61K 47/48176* (2013.01); *A61K 47/48207* (2013.01); *A61K 47/48338* (2013.01); *C08G 83/003* (2013.01)

(58) Field of Classification Search
CPC .. C08G 83/003; C08G 83/004; A61K 47/482; A61K 47/48207
USPC .......................................................... 525/329
See application file for complete search history.

(56) References Cited

U.S. PATENT DOCUMENTS 5,037,883 A * 8/1991 Kopecek et al. ............. 525/54.1
7,919,076 B2 * 4/2011 Ulbrich et al. ............. 424/78.17

(Continued)

OTHER PUBLICATIONS

Wang et al. Biomacromolecules, vol. 1, No. 3, 2000. DOI: 10.1021/bm0000236.*
Etrych et al. Journal of Controlled Release 132 (2008) 184-192. DOI: 10.1016/j.jconrel.2008.04.017.*

(Continued)

Primary Examiner — Mike M Dollinger
(74) Attorney, Agent, or Firm — Notaro, Michalos & Zaccaria P.C.

(57) ABSTRACT

The present invention relates to water-soluble high-molecular-weight polymer drug carriers and their conjugates with drugs, derived from dendrimers of the amidoamine and 2,2-bis(hydroxymethyl)propanoic types, the amino and hydroxy end groups of which are attached to semitelechelic copolymers of N-(2 hydroxypropyl)methacrylamide (HPMA) through biodegradable spacers. The polymer carriers and conjugates enable targeted transport notably of anticancer drugs into solid tumors in which biodegradation, the associated controlled drug release and subsequent elimination of polymer carrier from the organism are provided. The polymer carrier conjugated with a cancerostatic for use in targeted therapy of human tumors.

16 Claims, 5 Drawing Sheets

(56) References Cited

U.S. PATENT DOCUMENTS

| | | | |
|---|---|---|---|
| 8,603,990 B2* | 12/2013 | Etrych et al. | 514/34 |
| 2002/0123609 A1* | 9/2002 | Frechet et al. | 528/403 |
| 2005/0271615 A1* | 12/2005 | Shabat et al. | 424/78.3 |
| 2009/0041825 A1* | 2/2009 | Kotov et al. | 424/423 |
| 2011/0262991 A1* | 10/2011 | Raja et al. | 435/188 |
| 2012/0003322 A1* | 1/2012 | Sousa-Herves et al. | 424/501 |
| 2012/0296048 A1* | 11/2012 | Etrych et al. | 525/329.4 |

OTHER PUBLICATIONS

Kojima et al. Macromolecules, vol. 36, No. 7, 2003. DOI: 10.1021/ma025617a.*

Uchegbu et al. Polymers in Drug Delivery. CRC Press, 2006. ISBN 9781420021677.*

Domb et al. Handbook of Biodegradable Polymers. CRC Press, Feb. 4, 1998. p. 124.*

* cited by examiner

SEQUENCE LISTING

<160> NUMBER OF SEQ ID NOS: 5

<210> SEQ ID NO 1

```
<211> LENGTH: 2
<212> TYPE: PRT
<213> ORGANISM: Artificial
<220> FEATURE:
<223> OTHER INFORMATION: Oligopeptide spacer

<400> SEQUENCE: 1

Gly Gly
1

<210> SEQ ID NO 2
<211> LENGTH: 3
<212> TYPE: PRT
<213> ORGANISM: Artificial
<220> FEATURE:
<223> OTHER INFORMATION: Oligopeptide spacer

<400> SEQUENCE: 2

Gly Phe Gly
1

<210> SEQ ID NO 3
<211> LENGTH: 3
<212> TYPE: PRT
<213> ORGANISM: Artificial
<220> FEATURE:
<223> OTHER INFORMATION: Oligopeptide spacer

<400> SEQUENCE: 3

Gly Leu Gly
1

<210> SEQ ID NO 4
<211> LENGTH: 4
<212> TYPE: PRT
<213> ORGANISM: Artificial
<220> FEATURE:
<223> OTHER INFORMATION: Oligopeptide spacer

<400> SEQUENCE: 4

Gly Leu Phe Gly
1

<210> SEQ ID NO 5
<211> LENGTH: 4
<212> TYPE: PRT
<213> ORGANISM: Artificial
<220> FEATURE:
<223> OTHER INFORMATION: Oligopeptide spacer

<400> SEQUENCE: 5

Gly Phe Leu Gly
1
```

DENDRITIC HIGH-MOLECULAR-WEIGHT POLYMER DRUG CARRIERS AND THEIR CONJUGATES WITH DRUGS ESPECIALLY FOR TREATMENT OF SOLID TUMOURS

TECHNICAL FIELD

The invention refers to water-soluble high-molecular-weight (HMW) dendritic polymer drug carriers and their conjugates with drugs enabling targeted transport of antitumour drugs into solid tumours, biodegradation, the associated controlled drug release and subsequent elimination of polymer carrier from the organism. The action of the polymer carrier conjugated with a cancerostatic is aimed at targeted therapy of human tumours.

BACKGROUND ART

Recently the drug development has been more and more aimed at search for drug forms enabling targeted action of active substance primarily at the site of the required therapeutic effect. The targeted active forms of drug find application with the substances whose side effects may lead to damage of healthy parts of the organism. The most topical concern is the danger of damaging healthy tissues and organs, endangering patients treated with cytostatics. The utilization of polymer materials, in particular water-soluble polymers as carriers for targeted transport of drugs is one of the significant possibilities of solution to the mentioned problem. Attachment of a cytostatic to water-soluble polymer with a covalent bond makes it possible to significantly enhance the solubility of drugs poorly soluble in water and to reduce pronouncedly their toxicity. The molecular weights of polymer-drug conjugates prevents rapid elimination of the drug from the organism by glomerular filtration, thus prolonging significantly its time of circulation in blood and also its total dwell time in the organism thus leading to enhanced biological utilizability of the drug. In addition, high molecular weight of the polymer conjugate leads to its higher accumulation in solid tumours due to the effect of enhanced permeability and retention (EPR) [Maeda 2000].

If a cancerostatic is attached to polymer carrier, this effect can be utilized for its targeted accumulation in tumour. In the last two decades, a number of systems have been developed that are based on utilization of the EPR effect for targeting drugs such as polymer micelles, liposomes or water-soluble polymer conjugates. Polymer micelles, in contrast to soluble polymer systems, are usually prepared by assembling amphiphilic diblock copolymers into HMW structures forming colloid solutions. The drug is attached to micelles mostly in their hydrophobic cores by physical (hydrophobic) interactions or covalent bonds [Kataoka 2001, Bae 2003, Bronich 1999]. In contrast to micelles of soluble systems accumulating in solid tumours, polymers are dispersed molecularly in aqueous media, adopting usually a shape of random coil, in which the drug is in contact with hydrophilic polymer. Many types of conjugates of cancerostatics with soluble polymers were studied, in which the drug was attached by hydrolytically labile ionic bonds or covalent bonds prone to enzymatic or common chemical hydrolysis. The mentioned systems can release the cancerostatic in its active form in tumor tissue or also in a specific way directly in the tumour cell. Among water-soluble systems, polymer conjugates prepared on the basis of N-(2-hydroxypropyl)methacrylamide (HPMA) copolymers belong to the most important. A number of them are actively directed into tumours by an attached targeting structure (antibodies, hormones and oligopeptides). [Duncan 1985, Říhová 2000, Kopeček 2001, Mrkvan 2005].

One of the main drawbacks preventing the use of HPMA copolymers as drug carriers in human medicine is their non-cleavable carbon chain and the associated limits of molecular weights utilizable for preparation of polymer carriers of molecular weights to those lower than 40,000-50,000 (below the renal threshold of the organism). Polymers of high molecular weights are not eliminated from the organism effectively and sufficiently and hence their use as drugs would lead to their accumulation in the organism. If a pronounced EPR effect, i.e. significant accumulation in solid tumours, it is necessary to work with polymers, including HPMA copolymers, with molecular weights highly above the exclusion limits [Seymour 1995, Noguchi 1998]. Therefore, it is important that the molecular weight of polymer carrier is sufficiently high, but the polymer can be degraded, after release of the active component, to fragments, which can be eliminated from the organism, e.g., by glomerular filtration. Recently, we have patented structures and biological activities of drugs using HPMA polymers and their associates with molecular weights above the limit of renal filtration. These were graft polymer carriers [Etrych patent CZ 298 945 B6, Etrych 2008] and polymer micelles [Chytil patent CZ PV 2006-207] based on HPMA copolymers, in which a cancerostatic was attached to polymers with covalent bonds, which are enzymatically or just hydrolytically labile, and, possibly, polymer chains were linked to graft structures through biodegradable, enzymatically and/or reductively cleavable spacers, namely oligopeptide GlyPheLeuGly or a disulfide bridge. An advantage of the systems containing cancerostatic doxorubicin (Dox) as active component was an enhanced antitumour activity verified in mouse models compared with original polymer systems containing the same drug. A disadvantage of the mentioned systems is a relatively broad distribution of molecular weights (polydispersity index $I_n$ ranging from 3 to 4), hence a not well defined system with a limited possibility of obtaining high molecular weights exceeding 200,000 g/mol. The subject of the invention is the structure and synthesis of a new HMW polymer drug with a narrow distribution of molecular weights ($I_n$~1.5–2.5) and with a defined biodegradable skeleton characterized by enhanced accumulation of the cytostatic in tumour and, also, after intracellular degradation, by elimination of the polymer carrier from the organism. Their structure emanates from a dendritic central part, bearing on dendritic branches polymer grafts containing a covalently attached drug. By choice of the number of grafts and their size, it is possible to obtain high molecular weights of the polymer (up to 1,400,000 g/mol). Similar systems were described previously [Wang 2000], a principial difference between the described system and that of the subject of the invention and the previously published systems consists in that the previously described systems do not have a simply degradable polymer skeleton and the drug is attached only through the enzymatically degradable GlyPheLeuGly oligopeptide sequence. For modification of dendrimer branch ends, poly(ethylene glycol) (PEG) [Gajbhiye 2009, Bai 2009] was often used. The main task of PEG in these systems was hindering potentially toxic amino groups of dendrimers; PEG does not serve here as a carrier of biologically active molecules. Similarly to the preceding case, the systems are not biodegradable. If they should not accumulate in the organism, their utilization is limited to low molecular weights up to 50,000 g/mol.

Use of dendrimers with other, often biodegradable polymers has been mentioned in the patent literature. Poly(amino acid)s were used for preparation of dendrimer-poly(amino acid) conjugates [Li patent WO03055935], where the conjugate was prepared by polymerization of N-carboxyanhydrides of a-amino acids with dendrimer initiators. In this case, the poly(amino acid) grafts bear a significant negative charge (poly(glutamic acid) and poly(aspartic acid)), a positive charge (polyarginine, polyhistidine, polylysine) or are hydrophobic and hence insoluble in body fluids. A drug, e.g. paclitaxel, is bound to the polymer through a covalent ester bond. Due to a high charge density on the system surface or its considerable hydrophobicity and insolubility, undesirable interactions with various tissues and accumulation in the organism (e.g. kidneys) may occur as it is typical, e.g., of negatively charged poly(amino acid)s [Rypáček 1982]. Nor attachment of a drug to the polymer with a covalent ester bond without a biodegradable spacer guarantees the release of the drug in its original active form. In systems utilizing poly (amino acid) grafts, only partial degradation of poly(glutamic acid) is proved, in which cleavage of a broad spectrum of low-molecular-weight fragments and amino acid derivatives of the drug, which are not necessarily biologically active, happens. Degradation of such systems is documented in literature only in a model system containing cathepsin B and the data on their degradation in vivo are incomplete.

An advantage of the system according to the present invention are the polymer grafts formed by an inert, uncharged, water-soluble polymer, non-interacting with the organism, based on HPMA copolymer, to which the drug is attached through intracellularly degradable spacers enabling controlled release of active drug in target cells and tissues. Another advantage of the system according to the invention is the unequivocally proved intracellular reductive or enzymatic degradation of the carrier skeleton to polymer products of inert water-soluble HPMA copolymer which can be eliminated from the organism by glomerular filtration. Thus the elimination of HMW polymer carrier from the organism, after transporting a cancerostatic to the tumour site is guaranteed.

In literature, other systems are described, in which hydrophilic chains of poly[N-(2-hydroxypropyl) methacrylamide], poly(N-vinylpyrrolidone), poly(ethylene glycol methacrylate, poly(N-isopropylacrylamide), polyacrylic acid, poly (methacrylic acid, poly(2-aminoethyl methacrylate], poly[N-(3-aminopropyl)methacrylamide], and poly[2-(dimethylamino)ethyl methacrylate] were attached to linear or star poly(E-caprolactone), poly(L-lactide), poly(D-lactide), poly(DL-lactide), and poly(glycolic acid) [Lele patent U.S. Pat. No. 7,018,655]. The authors show that the thus prepared systems form HMW systems are utilizable in drug transport. The systems form micelles or nanoparticles in solution thanks to the amphiphilic nature of their structure, containing, e.g., hydrophobic poly(ε-caprolactone) and a HPMA-based polymer. The drug in these systems is then sorbed by hydrophobic interaction, on the hydrophobic core of the system, which does not enable controlled release of the drug in dependence on external conditions and cannot prevent the drug release in the course of transport. Moreover, this system is in most cases loaded with problems similar to those of the system described in a patent [Li patent WO03055935], i.e. a surface charge and undesirable interactions in the organism.

In contrast to the above-mentioned system, that is, according to the invention, soluble in water and body fluids, without a possibility of aggregation, bearing a drug attached through a biodegradable spacer, which enables controlled release of the drug in target cells or tumour tissue.

In literature, also the systems are described utilizing poly (amidoamine) (PAMAM) dendrimers as carriers, e.g. for anti-inflammation drugs [Kurtoglu 2009], in which the drug (N-acetylcysteine) is bound to a dendrimer through a reductively cleavable disulfide bridge. In this system, PAMAM dendrimer serves as a carrier. Hence, due to the PAMAM, it is difficult to obtain a high molecular weight, which is important for passive targeting into the tumour tissue.

DISCLOSURE OF INVENTION

The object of the present invention is the structure and synthesis of new HMW polymer drug carriers with dendritic structures and their drug conjugates, which differ from the previously described systems by narrow distributions of molecular weights, well defined structure of the systems, biodegradable skeleton and simplified synthesis. The described polymer drugs are characterized by enhanced accumulation of a cytostatic in tumour and by intracellular degradation and the associated ability of the polymer carrier to be eliminated from the organism after drug release and fulfilling its task of a carrier.

The object of the HMW biodegradable polymer carriers according to the invention lies in that it consists of a central $G_0$ generation up to $G_6$ generation of dendritic poly(amidoamine) and 2,2-bis(hydroxymethyl)propanoic structure, to the amino or hydroxy groups of which semitelechelic N-(2-hydroxypropyl)methacrylamide (HPMA) are attached through polymer chain ends using biodegradable spacers.

As biodegradable spacers, which can be degraded in live organisms mainly in tissues or target cells, are used reductively cleavable disulfide bonds or enzymatically cleavable oligopeptide sequences. Molecular weight of the central dendritic structure as well as semitelechelic grafts are selected below the elimination limit of the organism (ca 50,000 g/mol for HMPA copolymers) so that, after degradation, all the carrier components could be eliminated from the organism by glomerular filtration. Enzymatically degradable oligopeptide sequences linking the dendrimer to a HPMA copolymer contain, preferably GlyLeuGly, GlyPheGly, GlyPheLeuGly and GlyLeuPheGly sequences.

Biodegradable spacers can be introduced into the carrier structure in three ways—by the reaction of amino or hydroxy groups at the ends of dendrimer branches using semitelechelic polymers containing degradable spacers, by the reaction of a semitelechelic polymer with a dendrimer the end groups of which were modified with a structure containing a biodegradable spacer or by introducing a reductively-cleavable disulfide bond into the conjugate structure by the reaction of an activated dendrimer thiol group with a thiol end group of a semitelechelic polymer.

An aspect of the invention is further a polymer carrier with a poly(amidoamine) dendritic structure in its central part, which is grafted onto the amino groups with a semitelechelic HPMA copolymer, the polymer grafts being attached to dendrimer through the polymer chain end via an amide bond and a biodegradable spacer. The polymer carrier has schematic structures I and II.

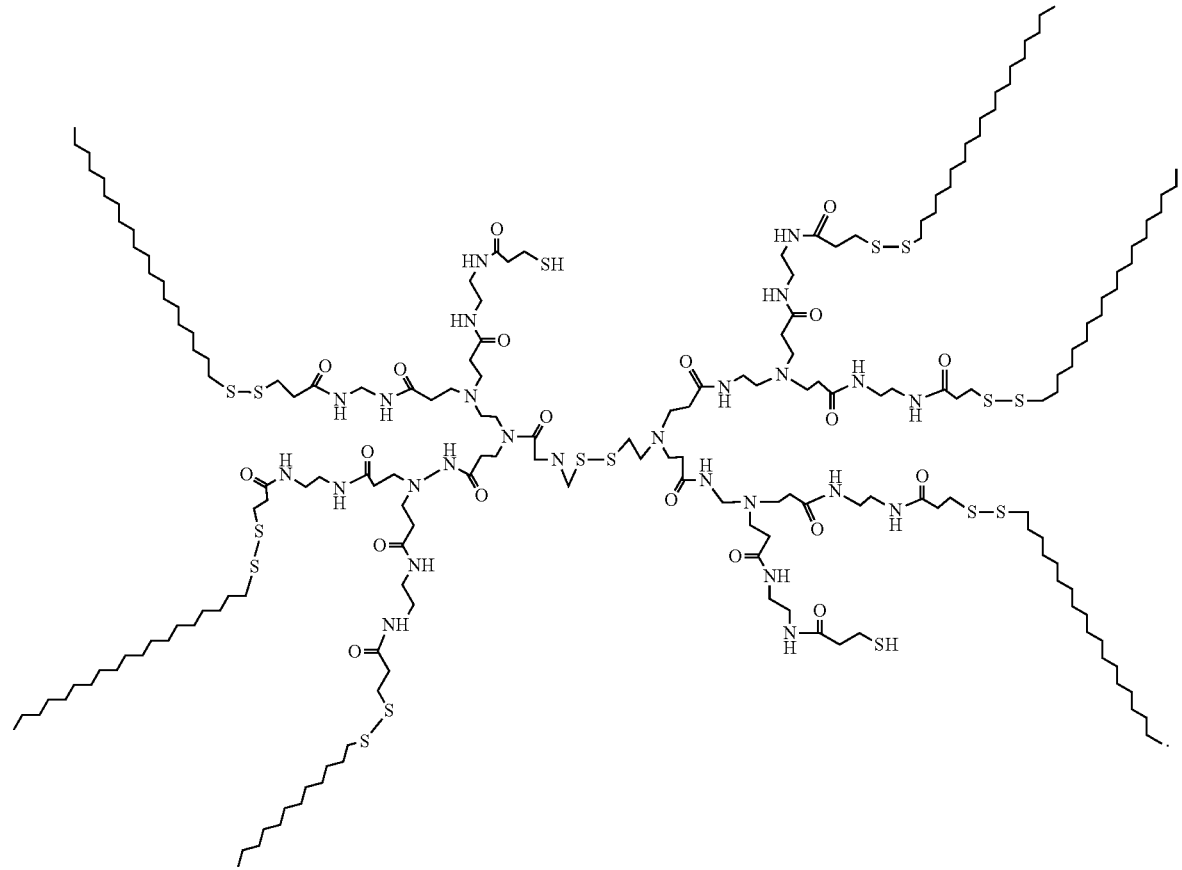

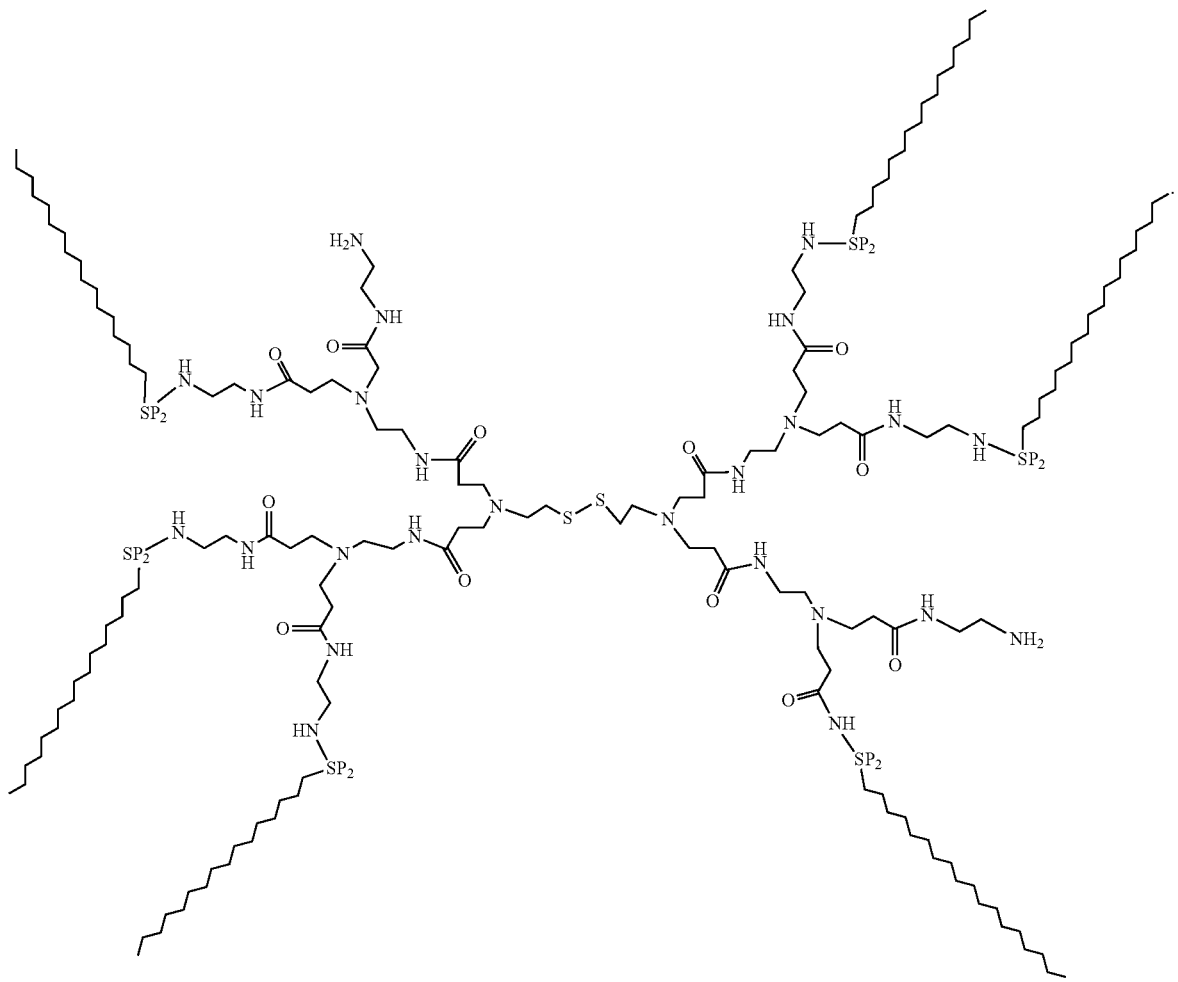

An object of the invention is further a polymer carrier, the central part of which is formed by a $G_o$ generation up to $G_6$ generation dendritic structure based on poly(amidoamine), containing 4-256 amino, pyridyldisulfanyl or carboxyl groups, with a core unit formed preferably by cysteamine, ethylenediamine, butane-1,4-diamine, hexane-1,6-diamine or dodecane-1,12-diamine.

The object of the present invention is further a polymer carrier, the central part of which is formed by a dendritic structure based on 2,2-bis(hydroxymethyl)propanoic acid, to which is bound through the hydroxy groups a semitelechelic HPMA copolymer, the polymer grafts being attached to the dendrimer through an ester bond and a biodegradable spacer. The polymer carrier has schematic structures III and IV.

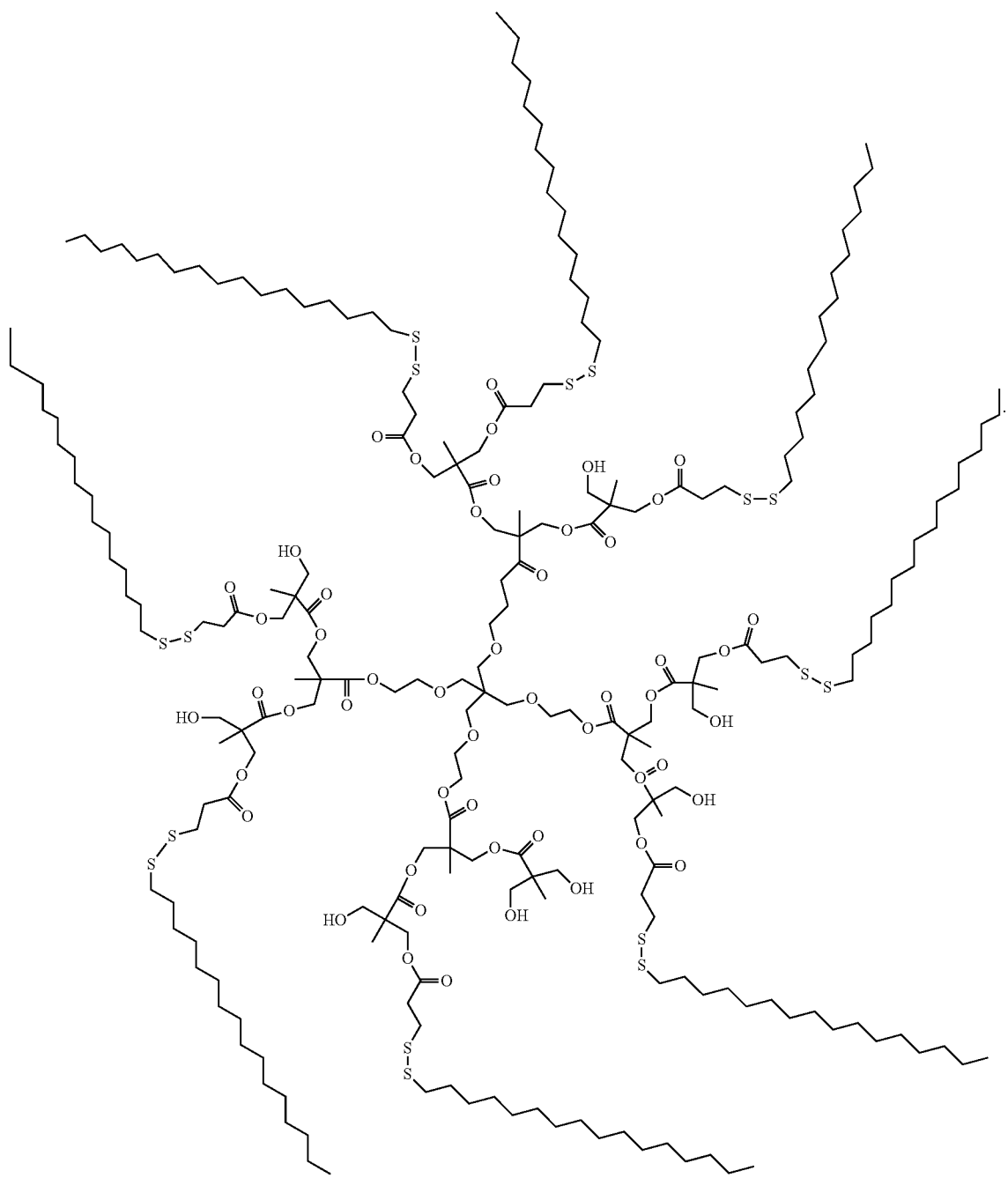

-continued
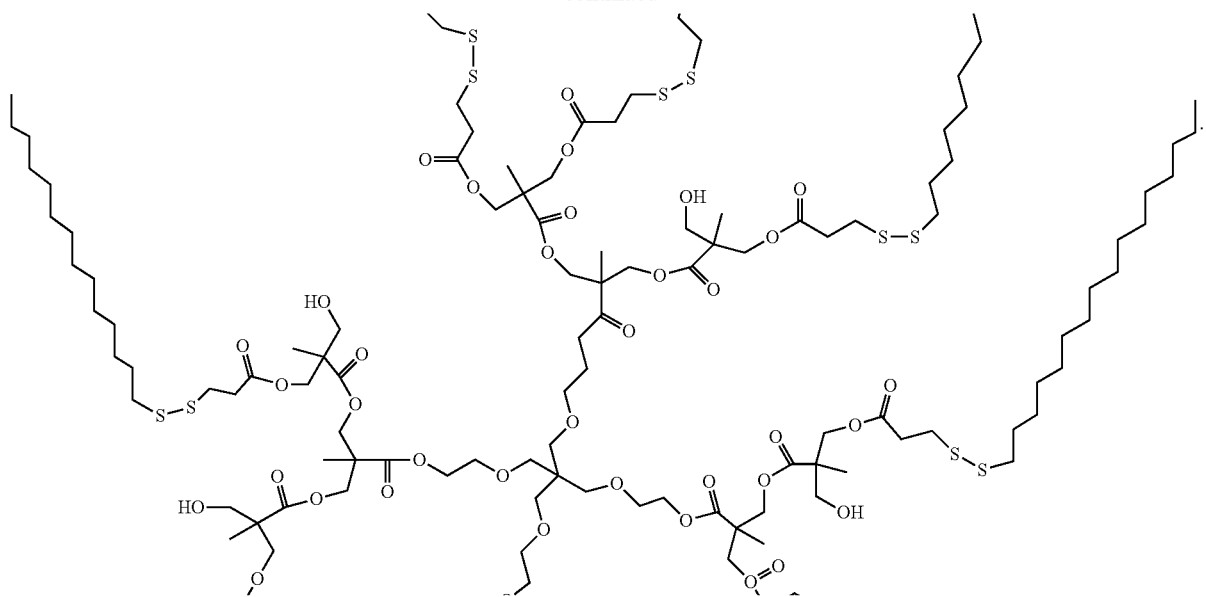

-continued

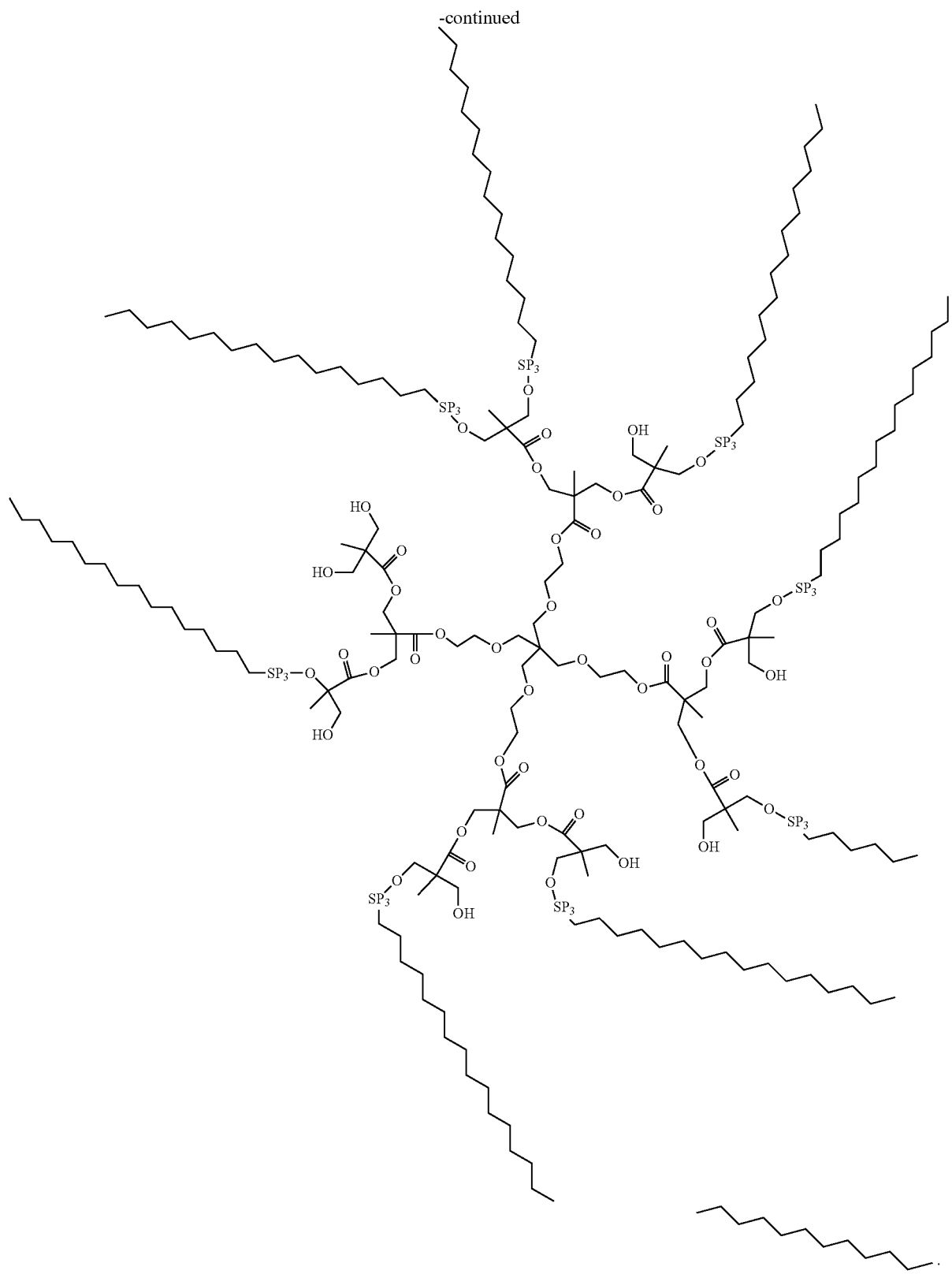

A further aspect of the present invention is a dendritic polymer carrier, the central part of which is formed by a dendritic structure based on 2,2-bis(hydroxymethyl)propanoic acid of generation one up to generation six, containing 8-256 hydroxy, pyridyldisulfanyl or carboxyl end groups.

An aspect of the dendritic polymer carrier according to the present invention is that it contains 2-28 grafts formed by a HPMA copolymer containing 0.5-8 mol % of monomer units of methacryloylated amino acid hydrazide of $SP_1$, where the aminoacyl is selected preferably from the group β-alanyl, 6-aminohexanoyl (AH), 4-aminobenzoyl and/or the complex acyl SP$_2$ derived from oligope hydrazides GlyGly, GlyPheGly, GlyLeuGly, GlyLeuPheGly and GlyPheLeuGly.

The invention further includes a HMW polymer carrier, in which polymer grafts are attached to the central poly(amidoamine) dendritic part through a biodegradable bond containing a disulfide or a biodegradable oligopeptide. The oligopeptide according to the invention is selected preferably from the group of enzymatically degradable oligopeptides GlyLeuGly, GlyPheGly, GlyPheLeuGly and GlyLeuPheGly.

A further object of the invention is a HMW polymer conjugate with a drug, consisting of a dendritic polymer carrier according to the present invention and a drug attached to the carrier through a hydrolytically-cleavable bond.

An aspect of the invention is also a HMW polymer conjugate, in which the drug is preferably a cancerostatic. A further aspect of the invention is a dendritic polymer conjugate, in which the cancerostatic is preferably doxorubicin, attached to the carrier through a hydrolytically-cleavable hydrazone bond.

A further aspect of the invention is that the HMW polymer conjugate according to the invention, which consists of a polymer carrier according to the invention and an amide-bound drug, in which 2-28 HPMA copolymer grafts containing 0.5-8 mol % of monomer units of methacryloylated oligopeptide hydrazides SP$_2$ with bound drug, preferably doxorubicin, attached through an amide bond at the end of oligopeptide sequence, the oligopeptide being selected from the group consisting of GlyPheGly, GlyLeuGly, GlyLeuPheGly and GlyPheLeuGly.

A further object of the invention is a conjugate of the HMW carrier derived from a dendritic structure and with doxorubicin, where the doxorubicin content is 1-25 wt. % The present invention also includes a pharmaceutical composition containing, as an active component, a HMW polymer conjugate derived from the dendritic structure according to the invention. The composition is intended for the use in the treatment of tumors, namely of solid tumours, some lymphoma types and leukaemia.

In polymer conjugates, the carrier bears a drug attached through a biodegradable bond, preferably pH-dependent hydrolytically-cleavable hydrazone bond or oligopeptide spacer cleavable with lysosomal enzymes. The polymer conjugate is constructed to obtain a sufficiently high molecular weight, which would significantly exceed the exclusion limit of the organism to provide a prolonged blood circulation time, a sufficiently high EPR effect and capture in solid tumor tissue. Molecular weight of the conjugate can be controlled by that of the semitelechelic polymers used in the synthesis, by the number of generations of the used dendrimer and substitution of dendritic end groups. Molecular weight of such dendritic system preferably ranges from 40,000 to 1,400,000 g/mol, the Dox content, both in polymer chains and in the resulting dendritic conjugate ranges from 1 to 25 wt % (0.3-8 mol % in the polymer).

The dendritic polymer conjugates according to the invention are predominantly intended for intravenous application (injection or infusion), but can be also applied into tumors or intraperitoneally. The polymer with a chemically bound cytostatic is stable in blood circulation, oligopeptide spacers or hydrazone bonds are relatively stable under physiological conditions of the bloodstream (pH 7.4). After extravasation and capture in solid tumors, the dissolved conjugate penetrates into tumor cells by pinocytosis thanks to the EPR effect. Due to a pH decrease from external pH 7.4 to intracellular 5-6, the hydrazone bond is hydrolyzed, the cytostatic is released in target cells and activated. Similarly, after entering tumor cells, disulfide bonds or oligopeptide spacers are cleaved in cytoplasm and cell lysosomes. The drug bound through an oligopeptide spacer and, at the same time, the polymer skeleton degrades to fragments, which can be eliminated from the organism. If, moreover, a PAMAM dendritic structure with cysteamine core is built-in in the conjugate, the core already contains biodegradable disulfide bonds enabling decomposition of the system in tumor cells to degradation products of lower molecular weights.

In contrast to the systems described in literature, the carrier according to the present invention, after fulfilling its function of a HMW passively targeted carrier, is degradable in the organism to well-soluble and biocompatible short polymer fragments. In a mildly acid reductive medium of the cell, disulfide bonds are reduced (according to literature, the glutathione concentration in cytoplasm of animal cells ranges between 1 and 5 mmol/l) and the HMW system decomposes to fragments of the original polymer, which can be eliminated from the organism. Similar carrier degradation should occur with the carriers containing polymer chains attached to the dendritic structure through enzymatically-cleavable oligopeptide sequences. In this case the polymer skeleton should be degraded by the action of lysosomal enzymes. The reality of the proposed mechanism of action of polymer conjugates according to the invention is documented by model release of doxorubicin from the polymer carrier and by degradation of dendritic polymers studied in medium modelling relations in the animal cell. The results of these tests, including tests for antitumor activity, are given in Examples of the present patent application.

The object of the invention are thus biodegradable HMW carriers of cancerostatics and conjugates of the carriers with selected cancerostatics, preferably doxorubicin, with pronounced cytotoxic and cytostatic effects on solid tumors.

The polymer carriers and their conjugates with drugs can be divided into the following groups:

Polymer carrier of type 1 is characterized in that the core of the system is formed by a poly(amidoamine)-based dendrimer core with the central part formed by cysteamine, ethylenediamine, butane-1,4-diamine, hexane-1,6-diamine or dodecane-1,12-diamine, with 4-256 end amino groups (see the structures in Schemes 11, 13 and 14) onto which 2-28 HPMA copolymer grafts with molecular weights 10,000-50,000 g/mol are attached through spacers containing reductively cleavable disulfide bonds characterized in that the copolymer grafts are selected from a group of semitelechelic HPMA copolymers with structures and composition given in Schemes 7-10.

Polymer carrier of type 2 is characterized in that the core of the system is formed by a dendritic structure based on 2,2-bis(hydroxymethyl)propanoic acid, with 8-256 hydroxy end groups (see the structures in Schemes 12 - 14) onto which 2-28 HPMA copolymer grafts with molecular weights 10,000-50,000 g/mol is attached through spacers containing reductively cleavable disulfide bonds characterized in that the polymer grafts are selected from the group of semitelechelic HPMA copolymers with structures and compositions given in Schemes 7 -10.

The type 3 polymer carrier is characterized in that the core of the system is formed by the same dendritic structure as in the case of polymer carrier of type 1, the semitelechelic polymer being attached through biodegradable oligopeptide sequences, GlyPheLeuGly, characterized in that the polymer graft is selected from a group of semitelechelic HPMA copolymers with structures and compositions given in Schemes 1-6.

Polymer carrier of type 4 is characterized in that the core of the system is formed by the same dendrimer as in the case of polymer carrier of type 2, the semitelechelic polymer being attached through biodegradable oligopeptide sequences, preferably GlyPheLeuGly, characterized in that the polymer graft is selected from a group of semitelechelic HPMA copolymers with structures and compositions given in Schemes 1-6.

The structures of polymer conjugates type 1-4 are identical with the structures of polymer carriers; however, a cancerostatic is bound to polymer grafts by purely hydrolytically-cleavable hydrazone bonds or enzymatically-cleavable amide bonds at the end of the oligopeptide sequence (spacer). Molecular weight of polymer conjugates range between 40,000 and 1,400,000 g/mol depending on the size of the dendritic moiety, length of the semitelechelic polymer and the degree of substitution.

Structures of Dendritic Polymer Carriers and Their Conjugates with Doxorubicin

The synthesis of polymer carriers and polyner conjugates with attached Dox according to the invention is carried out in several steps. It consists of synthesis of monomers (HPMA, methacryloylated oligopeptides with Dox bound as amide, methacryloylated derivatives of amino acids and oligopeptides terminated with hydrazide or Boc-protected hydrazide group), subsequent syntheses of polymer precursors (semitelechelic polymers with reactive end groups for bonding to central dendritic structure and bearing along the chains protected or unprotected hydrazide groups or drug moieties attached through an oligopeptide spacer) prepared by radical polymerization. Synthesis of monomers and semitelechelic polymer precursors was described in detail previously [Etrych patent CZ 298 945 B6, Etrych 2008]. Synthesis of semitelechelic polymers was performed by radical polymerization in the presence of a chain transfer agent (3-sulfanylpropanoic acid) (SPA) or by copolymerization initiated with a bifunctional azo initiator (3,3'-azobis(cyanoisovaleric acid) (ABIA), or 3,3'-[4,4'-azobis(4-cyano-4-methyl-1-oxobutane-4,1-diyl)]bis(thiazolidine-2-thione), ABIA-TT) or by a controlled radical polymerization (RAFT, reversible addition-fragmentation chain transfer) initiated with azobisisobutyronitrile and 4-cyano-4-thiobenzoylsulfanylpentanoic acid followed .by sodium borohydride reduction.

Semitelechelic copolymers are characterized in that they contain 85-99 mol % HPMA units, 1-15 mol % of units of methacryloylated Boc-protected amino acid hydrazides or oligopeptides or methacryloylated oligopeptides with an attached drug and a reactive group at the end of reactive chain. In the synthesis of carriers and conjugates, semitelechelic copolymers were used, containing the following reactive groups: carboxyl, carboxythiazolidinethione (TT), primary amino group, thiol and pyridyldisulfanyl (PDS). The structures of the polymers are given below in the Schemes showing the structures of polymers, carriers and conjugates. The following symbols are used:

(i) SP, for amino acid acyl in methacryloylated amino acid hydrazides, e.g. glycyl, β-alanyl, 6-aminohexanoyl (AH), 4-aminobenzoyl, and/or a complex acyl derived from oligopeptides GlyGly, GlyPheGly, GlyLeuGly, GlyLeuPheGly and GlyPheLeuGly;
(ii) $SP_2$ for complex acyl in methacryloylated amino acid amides derived from enzymatically degradable oligopeptide sequence containing, preferably, biodegradable oligopeptide sequences GlyLeuGly, GlyPheGly, GlyPheLeuGly and GlyLeuPheGly);
(iii) MA for methacryloyl
(iv) AE for 2-aminoethyl
(v) SP for sulfanylpropanoyl List of Copolymers Polymer 1

Copolymer of HMPA and methacryloylated amino acid hydrazides or oligopeptide hydrazides, the hydrazide groups being Boc-protected (—CONHNH-Boc), the copolymer contains reactive N-succinimidyl ester or carboxyl end chain group (Polymer 1a). The copolymer was prepared by copolymerization in the presence of chain transfer agent (sulfanylpropanoic acid, SPA). In the second step, the SPA(-COOH) chain-end group was transformed into N-succinimidyl ester by the N-hydroxysukcinimide/DCC reaction.

Scheme 1: Structure of
poly(HPMA-co-MA—SP1—NHNH—Boc)—SPA—OSu
(Polymer 1a)

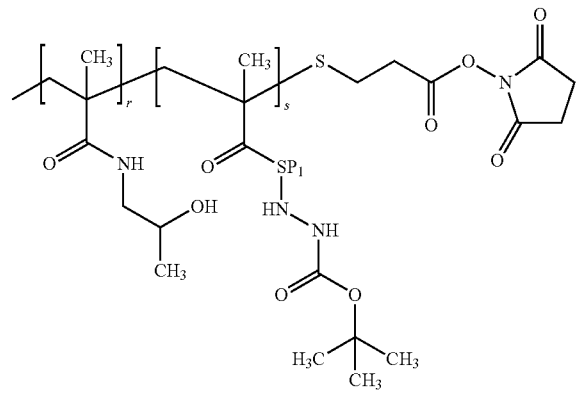

HPMA copolymer with methacryloylated amino acids or oligopeptides terminated with Boc-protected hydrazide group, the copolymer contains reactive carbonylthiazolidine-2-thione chain-end group (Polymer 1b) or N-succinimidylester chain-end group (Polymer 1c).

Scheme 2: Structure of
poly(HPMA-co-MA—SP1—NHNH—Boc)—TT
(Polymer 1b) or
poly(HPMA-co-MA—SP1—NHNH—Boc)—OSu
(Polymer 1c)

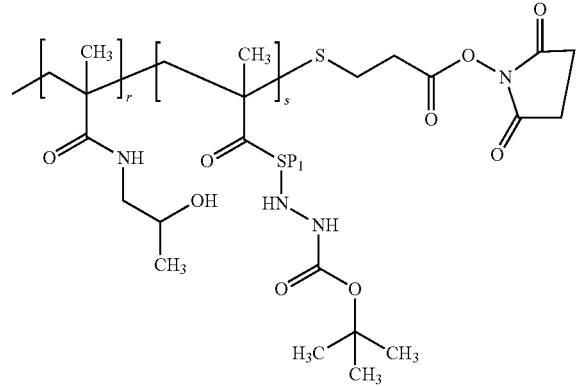

—R = 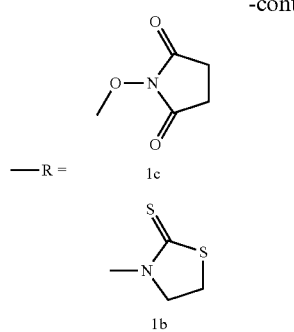

1c

1b

HPMA copolymer with methacryloylated amino acids or oligopeptides terminated with Boc-protected hydrazide group and chain-end N-succinimidyl ester group of a biodegradable oligopeptide, e.g. GlyPheLeuGly, generally SP2 (Polymer 1d), was prepared by two-step synthesis. In the first step, N-succinimidyl ester of poly(HPMA-co-MA-AH-NHNH-Boc)-SPA-OSu copolymer reacted with the amino group of oligopeptide GFLG. In the second step, the carboxyl chain-end group of the prepared copolymer poly(HPMA-co-MA-AH-NHNH-Boc)-SPA-GFLG-COOH was transformed into the N-succinimidyl ester by the N-hydroxysuccinimide/DCC reaction.

Scheme 3: Structure of
poly(HPMA-co-MA—SP1—NHNH—Boc)-SPA—SP2—OSu
(Polymer 1d)

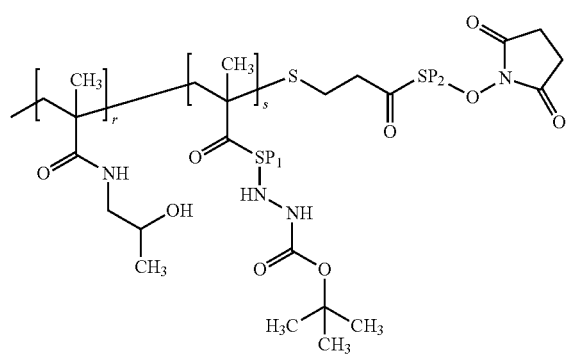

Copolymers of HPMA and methacryloylated oligopeptides with amide group-bound drug were prepared by radical polymerization of HPMA carried out in the presence of SPA as chain transfer agent. The copolymers are terminated with carboxyl groups or N-succinimidyl ester (Polymer 1e). The copolymers were prepared by copolymerization in the presence of chain transfer agent SPA. In the second step, the carboxyl end group was transformed into the N-succinimidyl ester by the N-hydroxysuccinimide/DCC reaction.

Scheme 4: Structure of
poly (HPMA-co-MA—SP2—Dox)—SPA—OSu
(Polymer 1e)

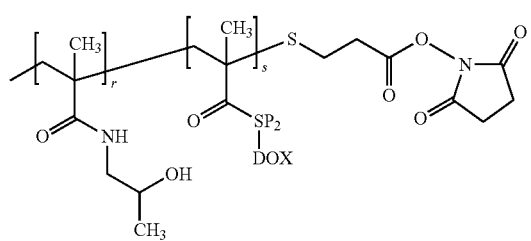

A copolymer of HPMA and methacryloylated oligopeptides with an amide bond-bound drug terminating with carbonylthiazolidine-2-thione end group (Polymer 1f) was prepared by radical polymerization of the corresponding monomers initiated with ABIA-TT. The copolymer terminated with N-succinimidyl ester group was prepared in a similar way under initiation with ABIA-TT and subsequent activation of the carboxyl chain-end group with N-hydroxysuccinimide (Polymer 1g).

Scheme 5
Structures of poly(HPMA-co-MA-SP2-Dox)-TT
(Polymer 1f and Polymer 1g)

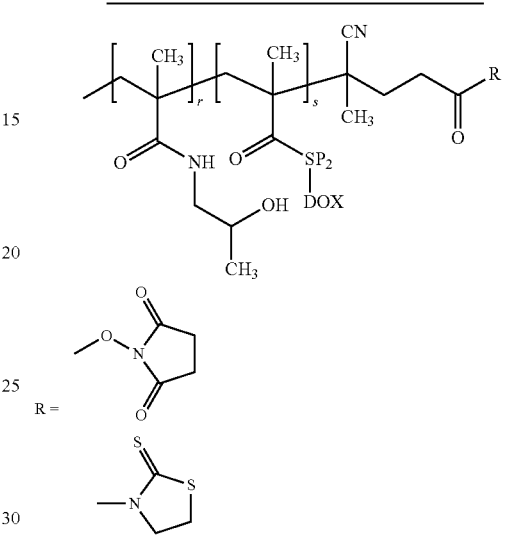

Copolymers of HPMA and methacryloylated oligopeptides with an amide-bound drug, with chain-end N-succinimidyl ester of biodegradable oligopeptide (e.g.GlyPheLeuGly), generally SP2 (Polymer 1h), were prepared by two-step snthesis. In the first step, succinimidyl ester of copolymer poly(HPMA-co-MA-SP2-Dox)-SPA-OSu reacted with amino group of the oligopeptide. In the second step, the carboxyl chain-end group of the prepared copolymer poly(HPMA-co-MA-SP2-Dox)-SPA-GFLG-COOH were transformed into the N-succinimidyl ester by the N-hydroxysuccinimide/DCC reaction.

Scheme 6: Structure of
poly(HPMA-co-MA—SP2—Dox)—SPA—SP2—OSu
(Polymer 1h)

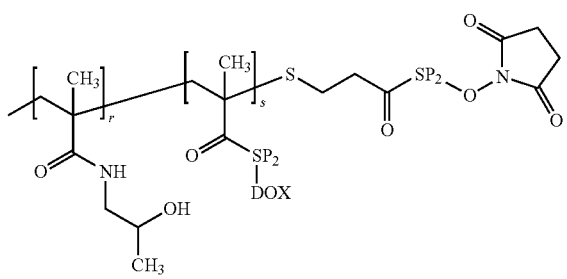

Polymers 2

The basic copolymer of HPMA and methacryloylated amino acid or oligopeptide hydrazide, the hydrazide groups being Boc-protected, with the thiol-terminated main chain was prepared by RAFT copolymerization of HPMA and relevant comonomer and subsequent reduction with sodium borohydride (Polymer 2z).

Scheme 7
Structure of poly(HPMA-co-MA—SP1—NHNH—Boc)—SH
(Polymer 2z)

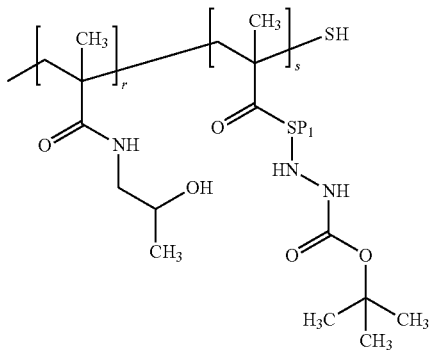

HPMA copolymers of HPMA and methacryloylated amino acid or oligopeptide hydrazides, the hydrazides being N-Boc-protected, with the thiol group-terminated main chain was prepared by the reaction of succinimidyl ester of Polymer 1a with 2-(2-pyridyldisulfanyl)ethylamine (PDEA) and subsequent reduction with dithiothreitol (DTT) (Polymer 2a).

Scheme 7b: Structure of
poly(HPMA-co-MA—SP1—NHNH—Boc)—SPA—AE—SH
(Polymer 2a)

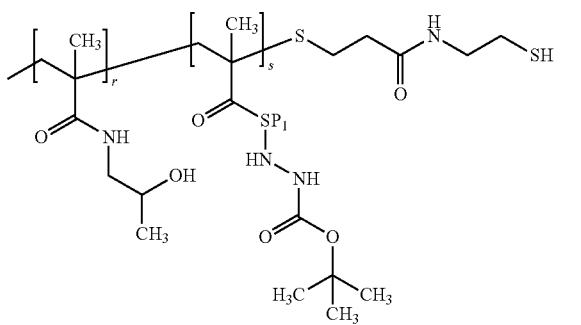

The copolymer of HPMA and methacryloylated amino acid or oligopeptide hydrazide, the hydrazide groups being Boc-protected, with the thiol group-terminated main chain was prepared by the reaction of activated chain-end carboxyl groups of polymers 1b and 1c with PDEA and subsequent reduction with DTT (Polymer 2b).

Scheme 8: Structure of
poly(HPMA-co-MA—SP1—NHNH—Boc)—AE—SH
(Polymer 2b)

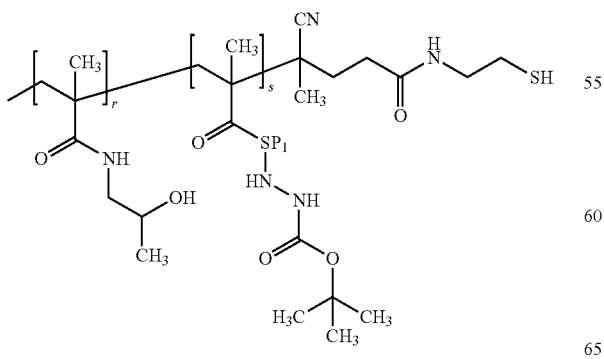

Copolymer of HPMA and methacryloylated oligopeptides with amide-bound drug, with the thiol group-terminated main chain was prepared by the reaction of succinimidyl ester chain-end groups of Polymer 1e with PDEA and subsequent reduction with DTT (Polymer 2c).

Scheme 9: Structure of
poly(HMPM-co-MA—SP2—Dox)—SPA—AE—SH
(Polymer 2c)

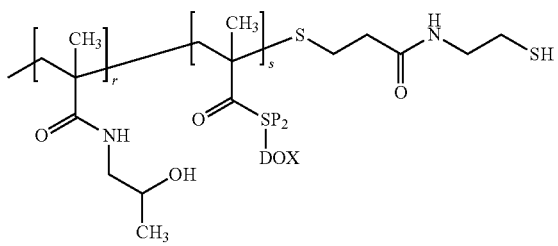

Copolymer of HPMA and methacryloylated oligopeptides with amide-bound drug, with the thiol group-terminated main chain was prepared by the reaction of activated carboxyl chain-end groups of Polymer 1f and Polymer 1g with PDEA and subsequent reduction with DTT (Polymer 2d).

Scheme 10: Structure of
poly(HMPM-co-MA—SP2—Dox)—AE—SH
(Polymer 2d)

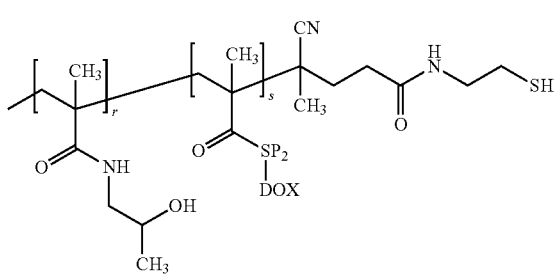

Dendrimer

Zero to six generation of dendritic structures was used as central parts in polymer conjugates. Preferably PAMAM dendrimers with cysteamine, ethylenediamine, butane-1,4-diamine, hexane-1,6-diamine or dodecane-1,12-diamine core units and with primary amino groups as end groups (Scheme 11)

Scheme 11: First generation of PAMAM dendrimer with the cysteamine core unit
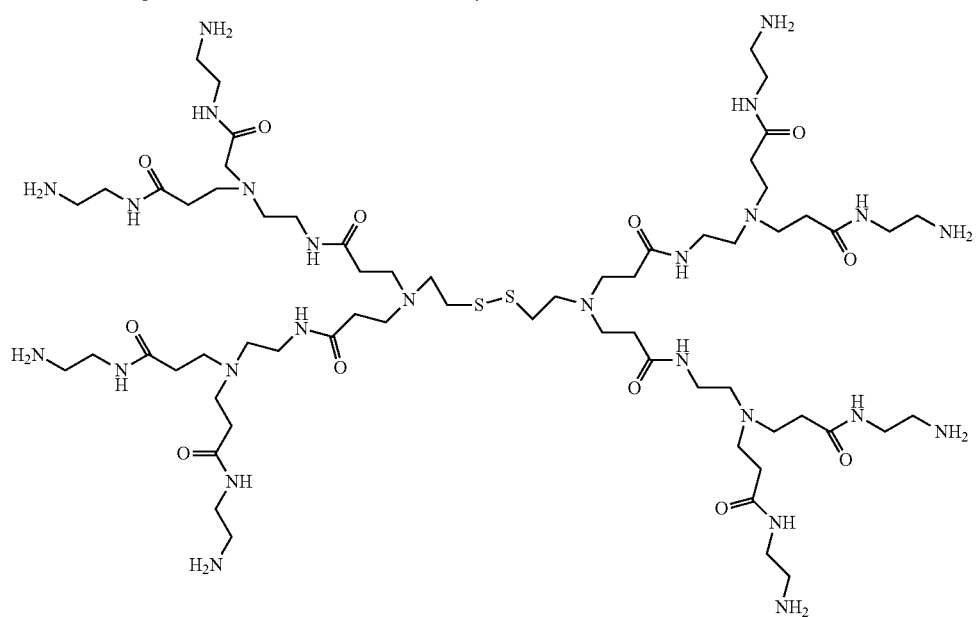
or
a dendrimer based on 2,2-bis(hydroxymethyl)propanoic acid (BPA) with hydroxy end groups were used (Scheme 12)
Scheme 12: First generation of dendrimer based on 2,2-bis(hydroxymethyl)propanoic acid
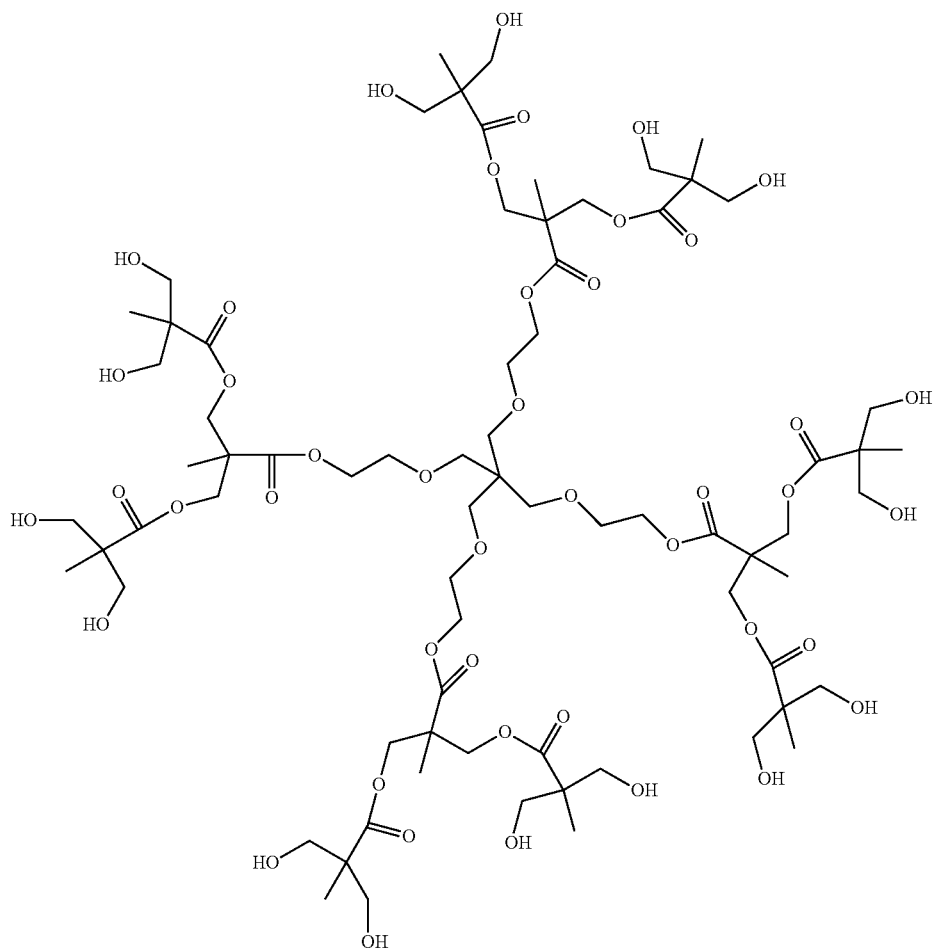

In the synthesis of some biodegradable polymer carriers and conjugates, the amino or hydroxy groups of PAMAM or BPA dendrimers were transformed into end pyridyldisulfanyl (PDS) groups (Scheme 13), before the reaction with a semi-telechelic polymer. In the amino groups-containing dendrimer the amino groups were modified by an oligopeptide SP2 cleavable with lysosomal enzymes (Scheme 14). The pyridyldisulfanyl groups were introduced by the reaction of amino groups with succinimidyl groups of N-succinimidyl [3-(2-pyridyldisulfanyl)]propanoate (SPDP) or by he reaction of hydroxy groups with 3-(2-pyridyldisulfanyl)]propionic acid using the DCC method. The oligopeptide was introduced by the reaction of amino or hydroxy groups of the dendrimer with Fmoc-protected oligopeptide using the DCC method.

Scheme 13: PAMAM dendrimer with PDS end group and BPA dendrimer with PDS end groups

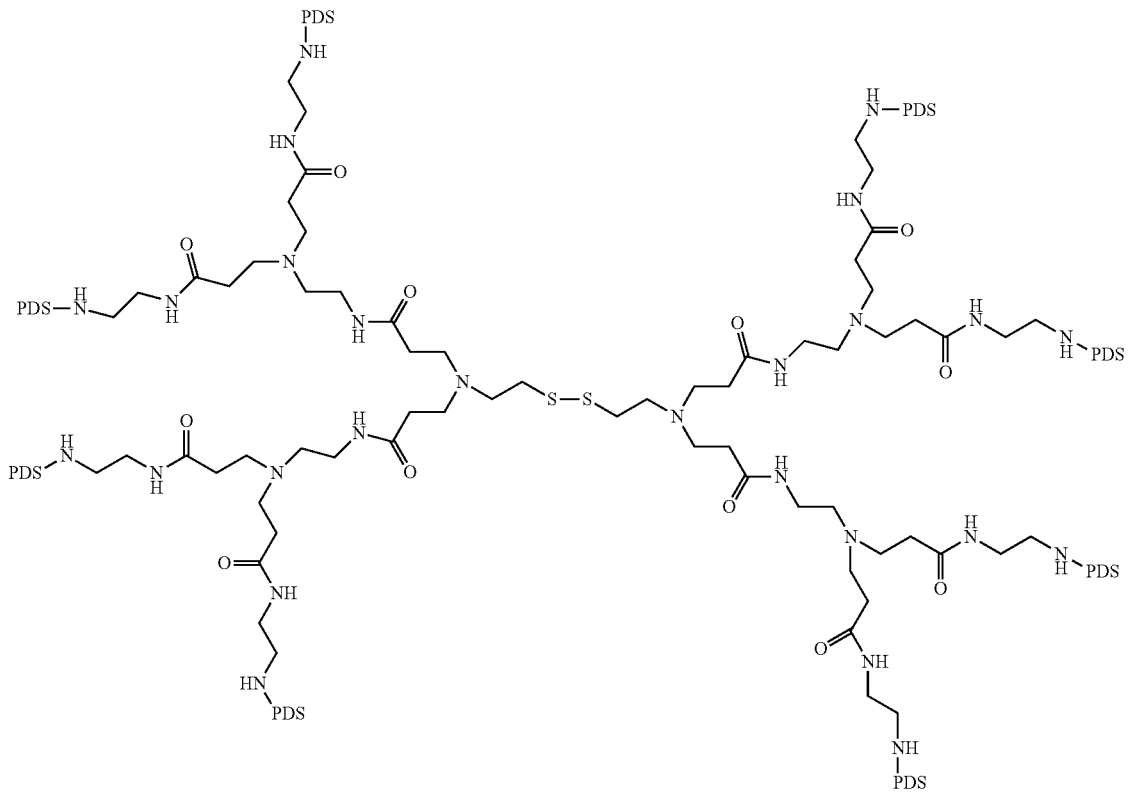

-continued
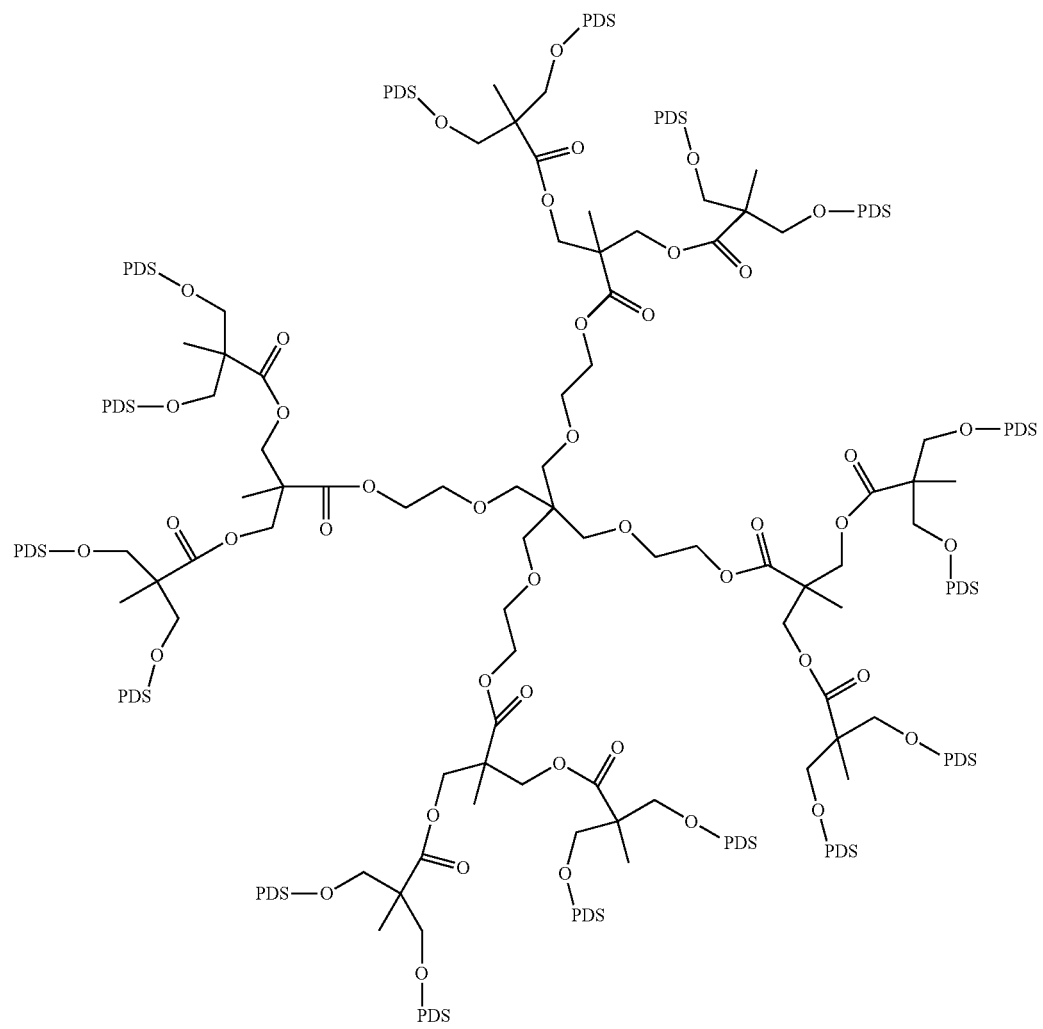
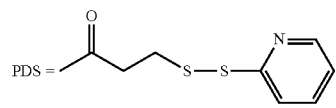

Scheme 14: PAMAM and BPA dendritics with attached oligopeptide GFLG
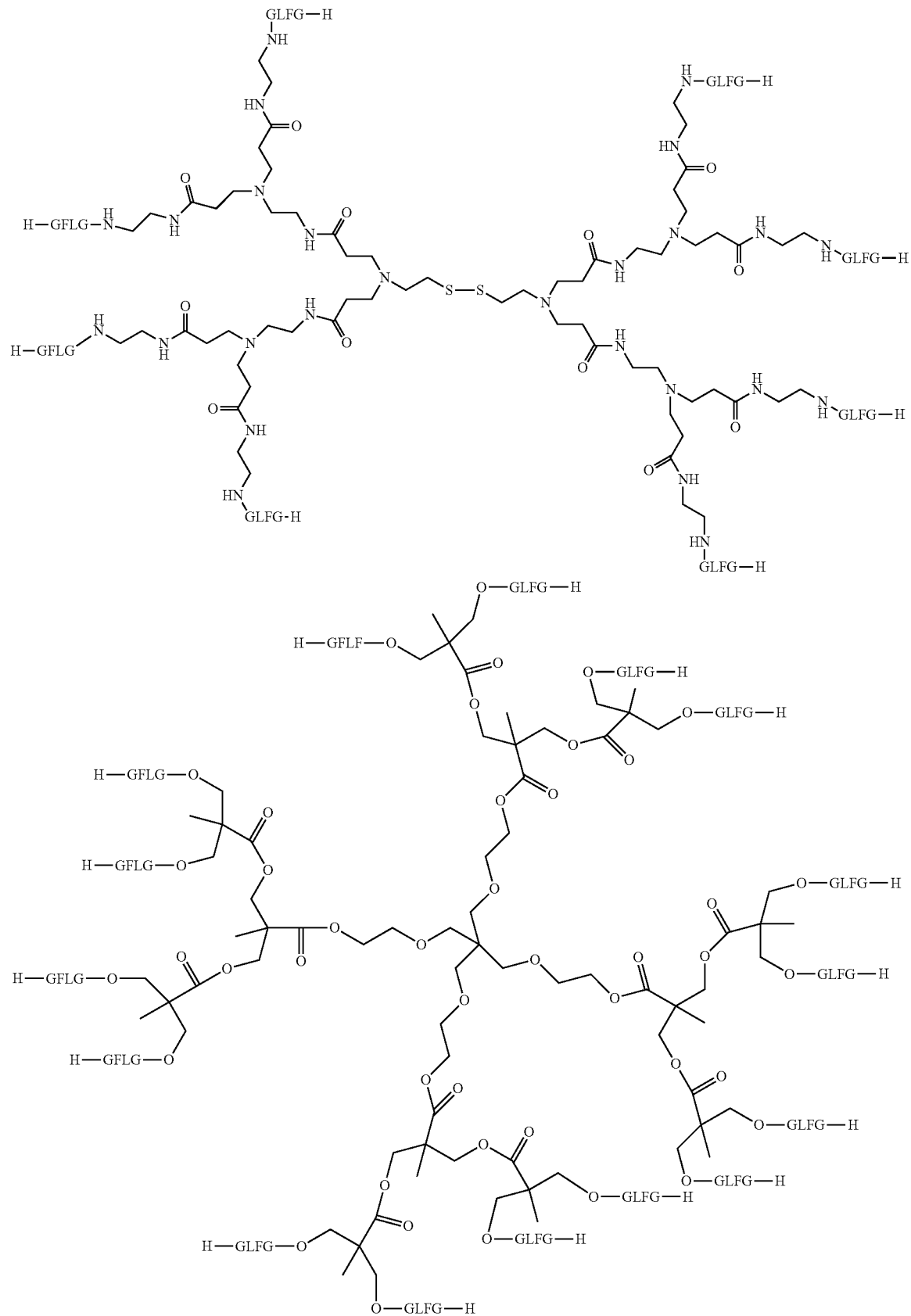

GLFG—H = 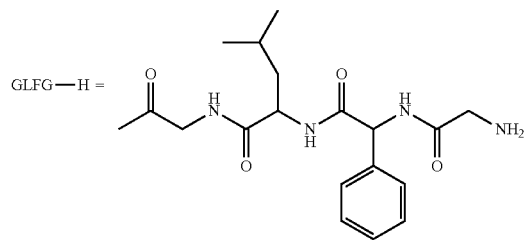

Hereinafter, polymer carrier is a HMW polymer without attached drug, containing a dendritic structure. Polymer conjugate is then a polymer carrier with attached drug. The drug, preferably doxorubicin, is attached to the carrier through a hydrazone bond, after removing the Boc protecting group. The attachment of Dox to the carrier is performed in methanol in the presence of acetic acid. In the case of amide-bound doxorubicin, the polymer conjugate is prepared by the reaction of semitelechelic copolymers bearing Dox with the corresponding dendrimer.

Due to the conjugate structure and mechanism of degradation of the polymer structure, the polymer conjugates according to the invention are divided into four basic groups:

Conjugate 1

Conjugate 1 consists of a central PAMAM dendritic structure to which polymer chains bearing drugs are attached through reductively degradable disulfide bonds. The drugs are attached to polymer chains with hydrazone or amide bonds (see Scheme 15)

Scheme 15: Conjugate 1 with a PAMAM dendrimer containing cysteamine core (first generation)

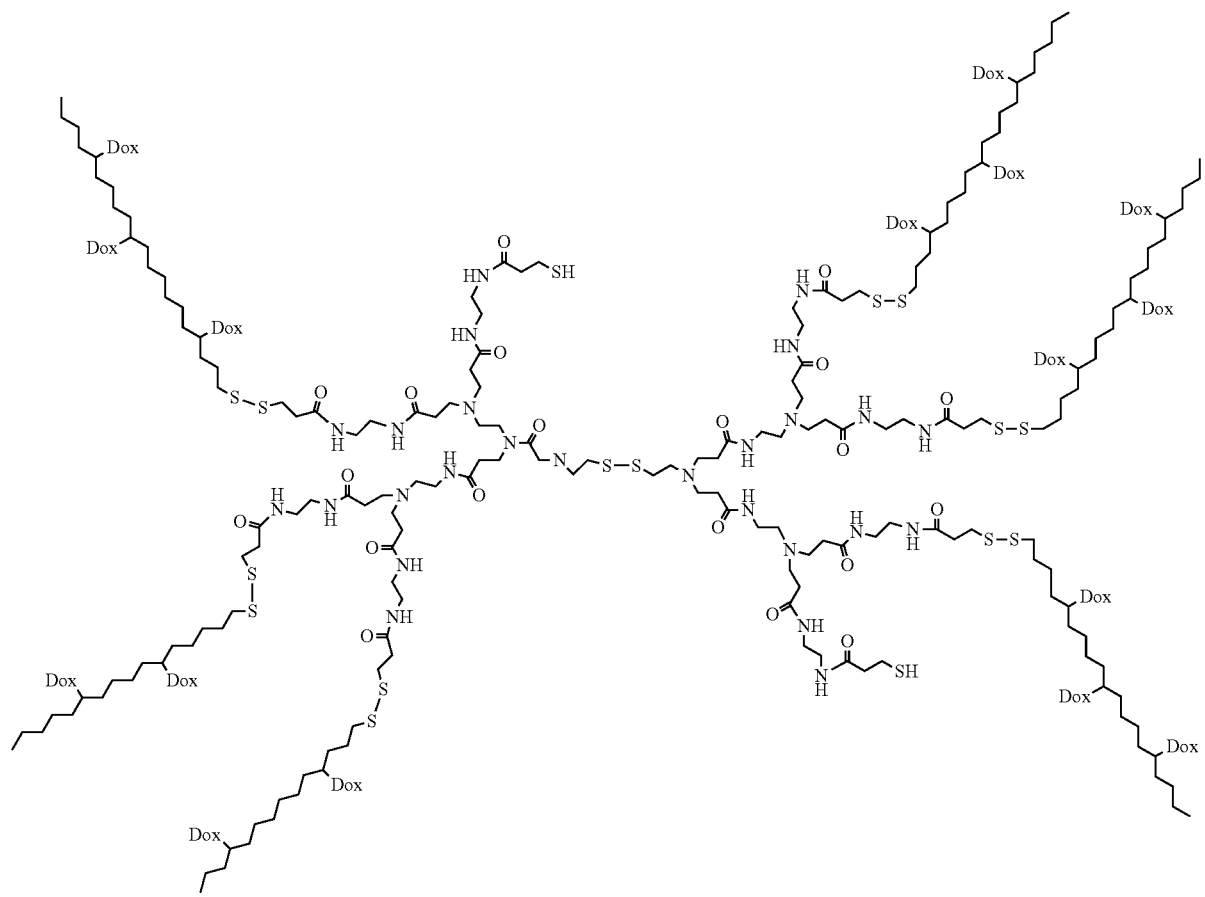

The zig-zag line denotes HPMA chain.

Conjugate 2

Conjugate 2 consists of a central BPA dendritic structure to which polymer chains bearing drugs are attached through reductively degradable disulfide bonds. The drugs are attached to polymer chains with hydrazone or amide bonds (see Scheme 16)

Scheme 16: Conjugate 2 with a BPA dendrimer (first generation) (the zig-zag line denotes HPMA copolymer chain)

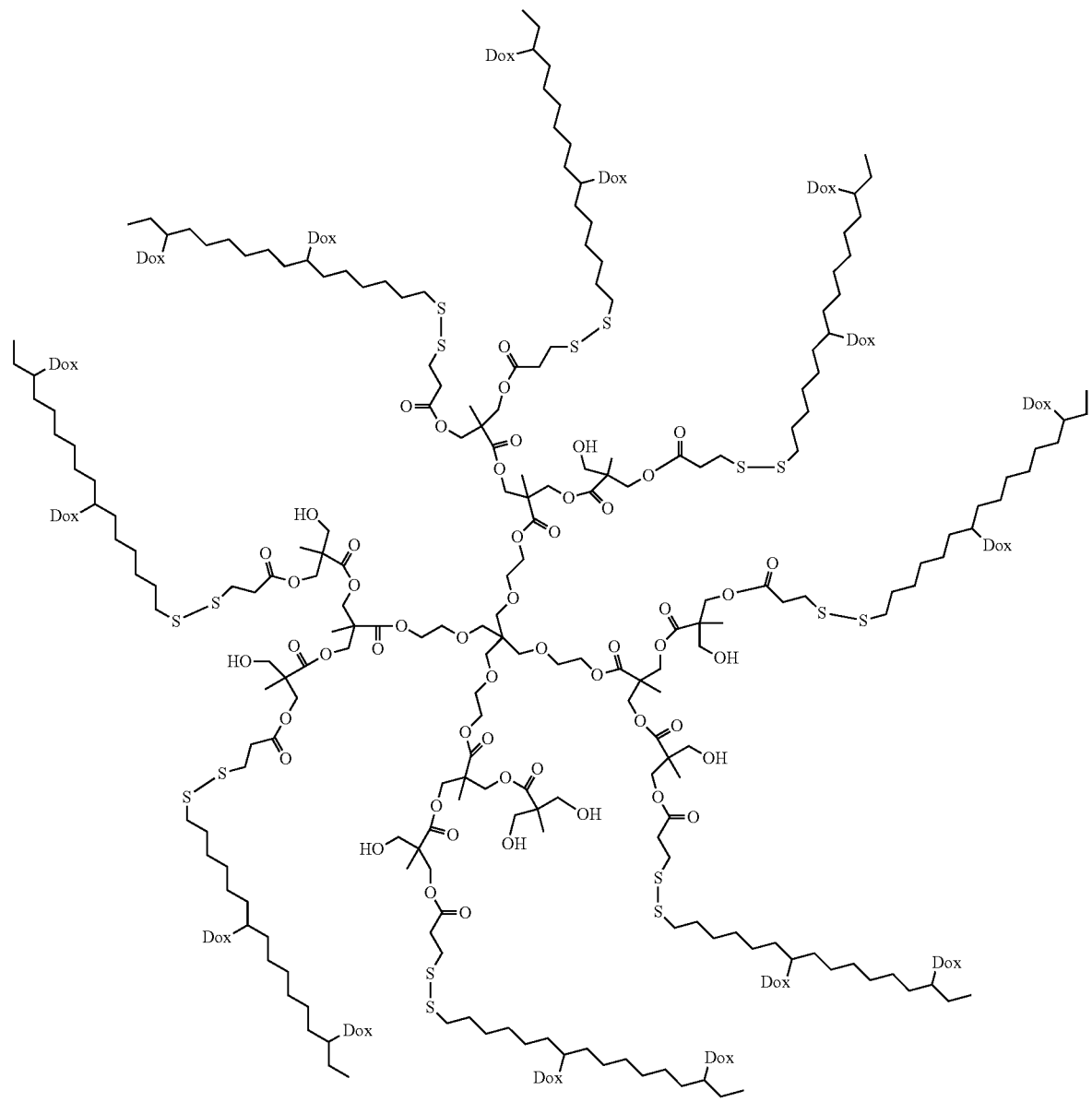

Conjugate 3

Conjugate 3 consists of a central PAMAM dendritic structure to which polymer chains bearing drugs are attached through enzymatically degradable oligopeptide. The drugs are attached to polymer chains with hydrazone or amide bonds (see Scheme 17)

Scheme 17: Conjugate 3 with PAMAM dendrimer (firts generation). The zig-zag line denotes HPMA copolymer chain.

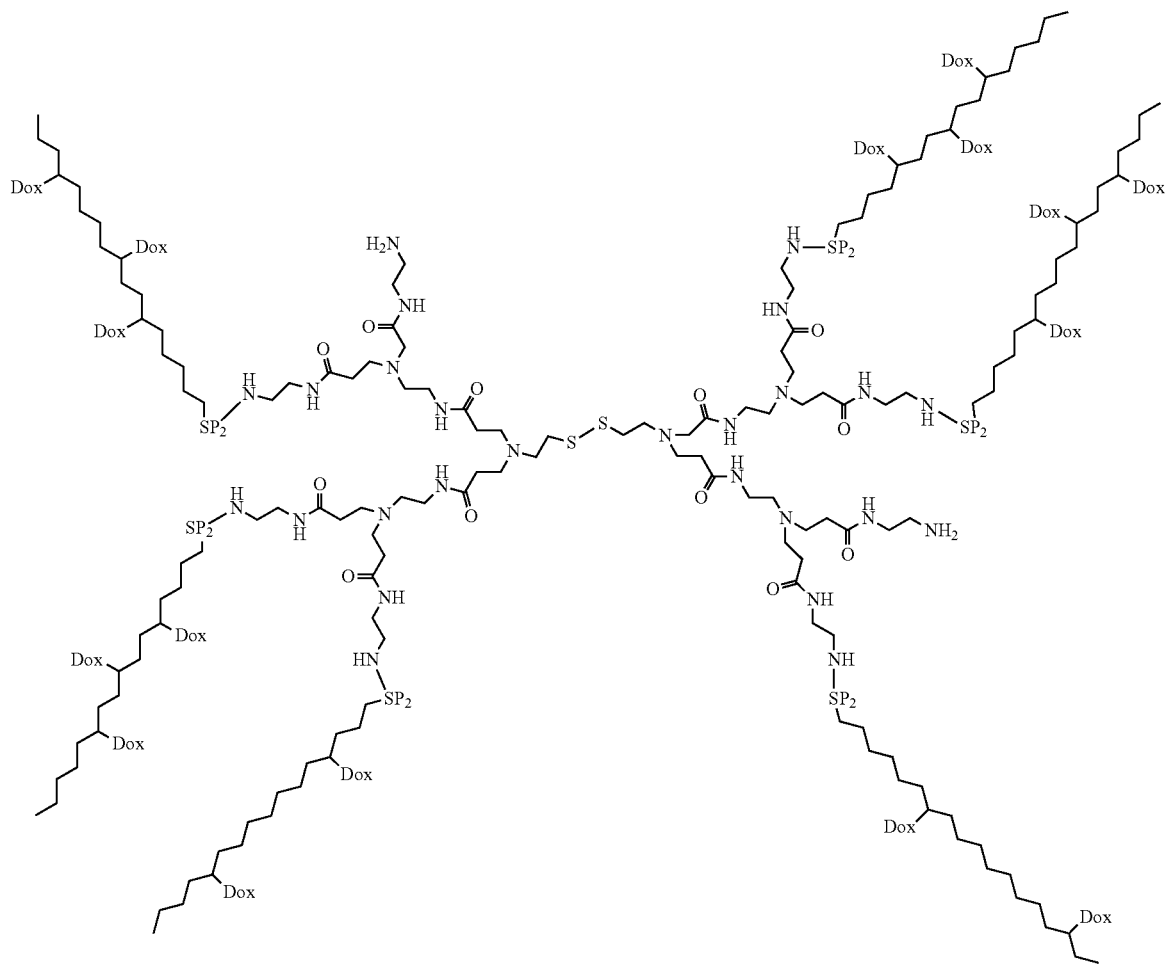

Conjugate 4

Conjugate 4 consists of a central BPA dendritic structure to which polymer chains bearing drugs are attached through enzymatically degradable oligopeptide. The drugs are attached to polymer chains with hydrazone or amide bonds (see Scheme 18)

Scheme 18: Conjugate 4 with a BPA dendrimer (first generation). The zig-zag line denotes HPMA copolymer chain.

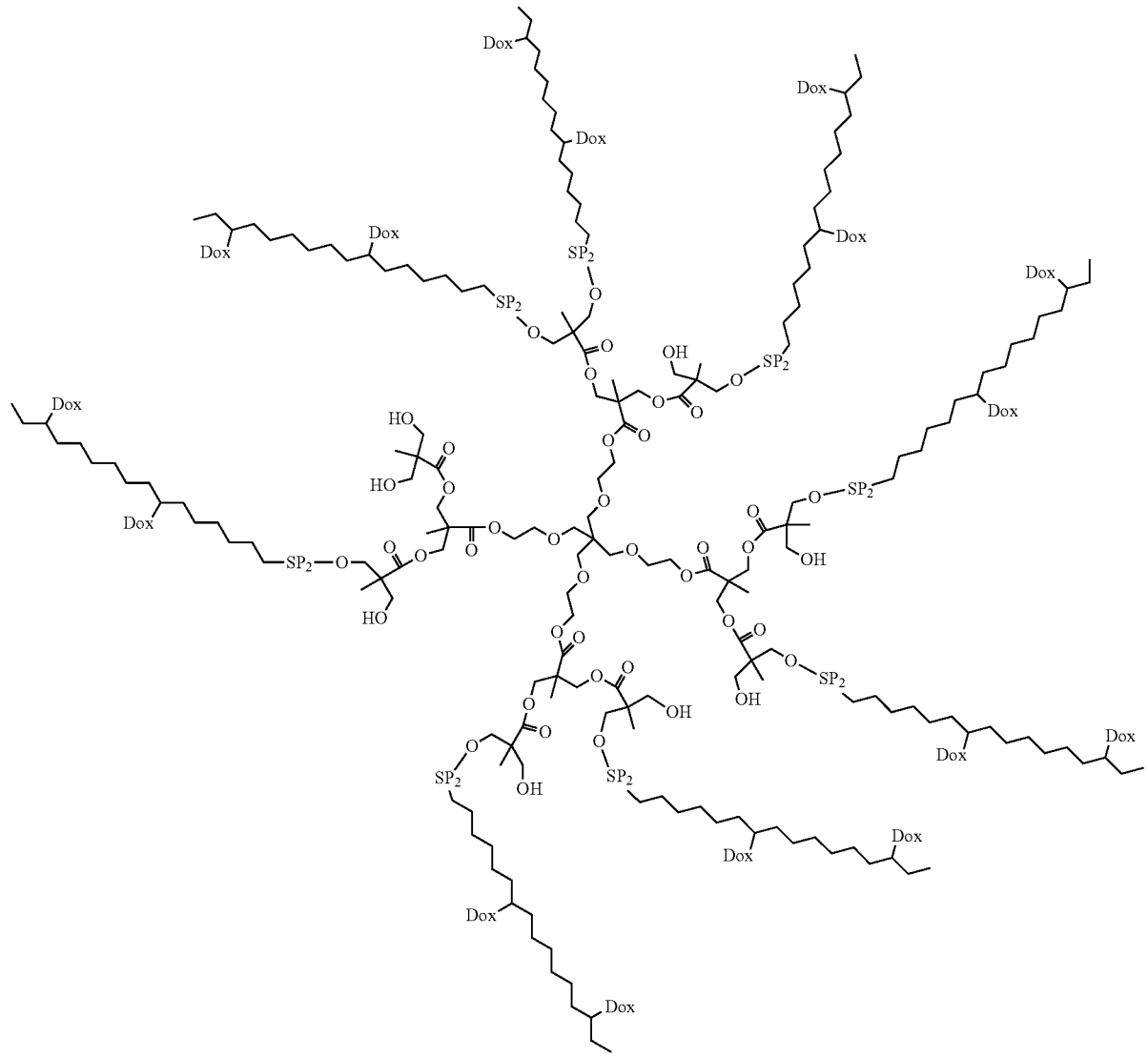

EXAMPLES OF CARRYING OUT THE INVENTION

Figure 1:
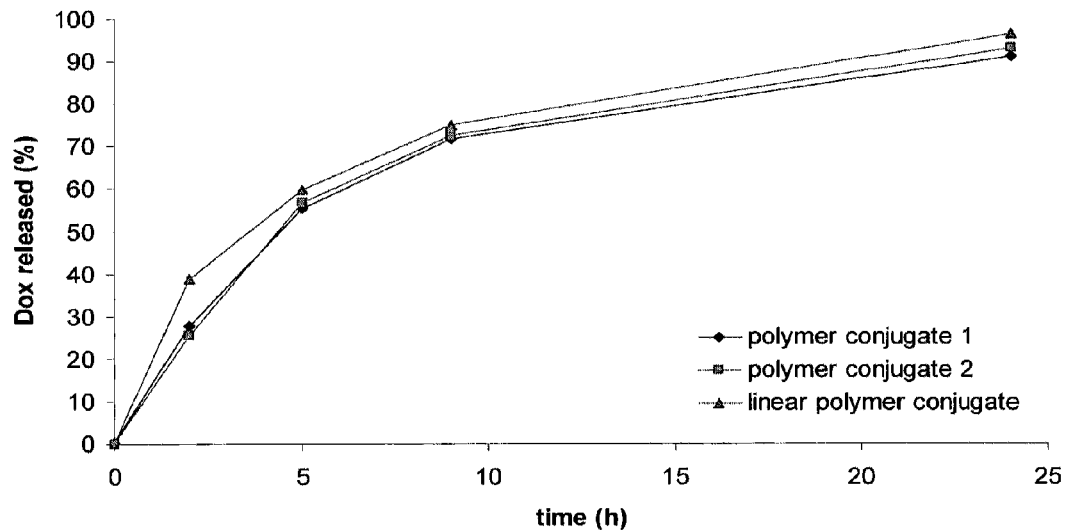
FIG. 1 shows the time dependence of the Dox released from dendritic polymer conjugates 1 and 2, and the linear polymer conjugate 3 at pH 5 (Dox is bound through hydrazone bonds) incubated in a buffer of pH 5 (modelling intracellular medium).

Examples of synthesis and properties of the conjugates

Examples of synthesis of intermediates and doxorubicin—polymer conjugates

Example 1

Synthesis of Semitelechelic Polymer Precursor (Using Chain Transfer Agent SPA) poly(HPMA-co-MA-AH-NHNH-Boc)-SPA-OSu (Polymer 1a)

Semitelechelic copolymer poly(HPMA-co-MA-AH-NHNH-Boc)-SPA-OSu was prepared by precipitation radical copolymerization of HPMA and MA-AH-NHNH-Boc in acetone at 50° C. in the presence of initiator 2,2'-azobis(2-methylpropionitrile) (AIBN) and chain transfer agent SPA. In some cases, the carboxy end groups were in the second step transformed into N-succinimidyl ester by the reaction with N-hydroxysuccinimide/DCC as described previously (Etrych, CZ patent 298 945 B6)

Example 2

Synthesis of Semitelechelic Polymer Precursor poly(HPMA-co-MA-AH-NHNH-Boc)-TT
(Polymer 1b)

Semitelechelic copolymer poly(HPMA-co-MA-AH-NHNH-Boc)-TT was prepared by solution radical copolymerization of HPMA and MA-AH-NHNH-Boc in DMSO at 60° C. initiated with ABIA-TT (Etrych, CZ Patent 298 945 B6)

Example 3

Synthesis of Semitelechelic Polymer Precursor poly(HPMA-co-MA-AH-NHNH-Boc)-OSu
(Polymer 1c)

Semitelechelic copolymer poly(HPMA-co-MA-AH-NHNH-Boc)-SPA-OSu was prepared by solution radical copolymerization of HPMA and MA-AH-NHNH-Boc in ethanol at 50° C. in the presence of initiator ABIA and subsequent activation of the carboxy chain-end groups by transformation into N-succinimidyl ester (Etrych, CZ Patent 298 945 B6)

Example 4

Synthesis of Semitelechelic Polymer Precursor poly(HPMA-co-MA-AH-NHNH-Boc)-SPA-GFLG-OSu (Polymer 1d)

Semitelechelic copolymer poly(HPMA-co-MA-AH-NHNH-Boc)-SPA-GFLG-OSu was prepared by a two-step synthesis. In the first step, N-succinimidyl ester of copolymer poly(HPMA-co-MA-AH-NHNH-Boc)-OSu reacted with amino group of oligopeptide GFLG. In some cases, the carboxy end groups of the prepared copolymer poly(HPMA-co-MA-AH-NHNH-Boc)-SPA-GFLG-COOH were, in the second step, transformed into N-succinimidyl ester by the reaction with N-hydroxysuccinimide/DCC as described previously (Etrych, CZ Patent 298 945 B6)

Example 5

Synthesis of Semitelechelic Polymer Precursor (Including Chain Transfer with SPA) poly(HPMA-co-MA-GFLG-Dox)-SPA-OSu (Polymer 1e)

Semitelechelic copolymer poly(HPMA-co-MA-GFLG-Dox)-SPA-OSu was prepared by precipitation radical copolymerization of HPMA and MA-GFLG-Dox in acetone at 50° C. in the presence of initiator AIBN and chain transfer agent SPA. The carboxy chain-end groups were, in the second step, transformed into N-succinimidyl ester groups by the reaction with N-hydroxysuccinimide/DCC. [Ulbrich 2000].

Example 6

Synthesis of Semitelechelic Polymer Precursor poly(HPMA-co-MA-GFLG-Dox)-TT
(Polymer 1f)

Semitelechelic copolymer poly(HPMA-co-MA-GFLG-Dox)-TT was prepared by solution radical copolymerization of HPMA and MA-GFLG-Dox in DMSO at 60° C., initiated with ABIA-TT.

220 mg (1.54 mmol) HPMA, 25 mg (0.025 mmol) MA-GFLG-Dox were dissolved in 1.7 ml DMSO and the solution was transferred into a polymerization ampoule, in which was 84 mg (0.170 mmol) ABIA-TT (4 wt %). Nitrogen was bubbled through the solution in an ampoule for 15 min; the ampoule was sealed and placed into a thermostat at 60° C. The initiator dissolved after 3 min at 60° C. After 6 h the reaction mixture precipitated into 50 ml of acetone-diethyl ether 2:1. The copolymer was dissolved in 3 ml of methanol and again precipitated into 50 ml of the same mixed solvent. The precipitated copolymer was filtered off and dried to constant weight.

Example 7

Synthesis of Semitelechelic Polymer Precursor poly(HPMA-co-MA-GFLG-Dox)-SPA-GFLG-OSu (Polymer 1h)

Semitelechelic copolymer poly(HPMA-co-MA-GFLG-Dox)-SPA-GFLG-OSu was prepared by a two-step synthesis described in preparation of poly(HPMA-co-MA-AH-NHNH-Boc)-SPA-GFLG-OSu (Example 4). In the first step, N-succinimidyl ester of copolymer poly(HPMA-co-MA-GFLG-Dox)-SPA-OSu reacted with the amino group of oligopeptide GFLG. The carboxy end of copolymer poly(HPMA-co-MA-AH-NHNH-Boc)-OSu with amino group of oligopeptide GFLG. In the second step, the carboxyl chain-end groups of the prepared copolymer poly(HPMA-co-MA-GFLG-Dox)-SPA-GFLG-COOH were transformed into N-succinimidyl ester by the reaction with N-hydroxysuccinimide/DCC.

Example 8

Synthesis of Semitelechelic Polymer Precursor—poly (HPMA-co-MA-AH-NHNH-Boc)-SPA-AE-SH (Polymer 2a)

Semitelechelic copolymer poly(HPMA-co-MA-AH-NHNH-Boc)-SPA-AE-SH was prepared by polymer-analogous reaction of copolymer poly(HPMA-co-MA-AH-NHNH-Boc)-SPA-OSu with a bifunctional reagent, 2-(2-pyridyldisulfanyl)ethylamine (PDEA), in DMSO and subsequent reduction with dithiothreitol (DTT) in 0.5 M phosphate buffer (0.1 M NaCl, pH 7.4).

8 mg PDEA.HCl (0.036 mmol) was dissolved in 0.5 ml DMSO and 6 $_1$.d ethyl(diisopropyl)amine (0.036 mmol) was added under intensive stirring. After 5 min, a solution of 300 mg of poly(HPMA-co-MA-AH-NHNH-Boc)-SPA-OSu (0.026 mmol TT groups) in 4 ml DMSO was added under intensive stirring at room temperature. After 2 h, the reaction mixture was diluted to 15 ml with methanol and the copolymer was purified by removing low-molecular-weight impurities by gel chromatography on a column filled with Sephadex LH-20 (methanol, RI detection). The polymer fraction was concentrated on a rotary vacuum evaporator to 6 ml and the copolymer was isolated by precipitation into 80 ml of acetone—diethyl ether 3:1. In the next step, 300 mg of the polymer with PDS groups (0.024 mmol) was dissolved in 5 ml of phosphate buffer and a solution of 18.5 mg DTT in 0.4 ml of distilled water was added. After 1 h the polymer was purified by removing low-molecular-weight impurities by gel filtration in water solution on a column filled with Sephadex G-25. The polymer was isolated by lyophilisation and stored under argon at −18° C.

Example 9

Synthesis of Semitelechelic Polymer Precursor—poly (HPMA-co-MA-AH-NFENH-Boc)-SPA-AE-SH (Polymer 2b)

Semitelechelic copolymer poly(HPMA-co-MA-AH-NHNH-Boc)-AE-SH was prepared by polymer-analogous reaction of copolymer poly(HPMA-co-MA-AH-NHNH-Boc)-OSu or poly(HPMA-co-MA-AH-NHNH-Boc)-TT with bifunctional reagent PDEA in DMSO and by subsequent reduction with DTT in 0.5 M phosphate buffer (0.1 M NaCl, pH 7.4) by the procedure described in Example 8.

Example 10

Synthesis of Semitelechelic Polymer Precursor—poly (HPMA-co-MA-GFLG-Dox)-SPA-AE-SH (Polymer 2c)

Semitelechelic copolymer poly(HPMA-co-MA-GFLG-Dox)-AE-SPK-SH was prepared by polymer-analogous reaction of copolymer poly(HPMA-co-MA-GFLG-Dox)-SPA-OSu with bifunctional reagent PDEA in DMSO and by subsequent reduction with DTT in 0.5 M phosphate buffer (0.1 M NaCl, pH 7.4) by the procedure described in Example 8.

Example 11

Synthesis of Semitelechelic Polymer Precursor—poly (HPMA-co-MA-GFLG-Dox)-AE-SH (Polymer 2d)

Semitelechelic copolymer poly(HPMA-co-MA-GFLG-Dox)-AE-SH was prepared by polymer-analogous reaction of copolymer poly(HPMA-co-MA-GFLG-Dox)-OSu or poly (HPMA-co-MA-GFLG-Dox)-TT with bifunctional reagent PDEA in DMSO and by subsequent reduction with DTT in 0.5 M phosphate buffer (0.1 M NaCl, pH 7.4) by the procedure described in Example 8.

Example 12

Synthesis of Dendrimer with PDS Groups

PAMAM or BPA dendrimers containing pyridyldisulfanyl groups (dendrimer-PDS) were prepared by the reaction of amino or hydroxy groups of dendrimers with succinimidyl groups of N-succinimidyl [3-(2-pyridyldisulfanyl)]propanoate (SPDP) or carboxyl groups of 3-(2-pyridyldisulfanyl)propanoic acid using the DCC method.

5 mg of second generation PAMAM dendrimer (0.026 mmol amino groups) was dissolved in 0.5 ml of methanol and, under constant stirring, a solution of 23 mg SPDP (0.071 mmol) in 0.5 ml methanol was added. After 2 h, the modified dendrimer was purified by removing low-molecular weight impurities by gel chromatography on a column filled with Sephadex LH-20 in methanol (RI detection). The fractions containing the dendrimer were concentrated on rotary vacuum evaporator to 1 ml and the dendrimer was isolated by lyophilisation from a mixture of methanol-water 1:3.

Example 13

Synthesis of a Dendrimer with Attached Oligopeptide

PAMAM or BPA dendrimers with attached oligopeptides (dendrimer-SP$_2$) containing amino end groups were prepared by the reaction of amino or hydroxy groups of dendrimers with carboxyl groups of N-Fmoc-protected oligopeptides in the presence of condensation reagent DCC.

40 mg of N-Fmoc-protected oligopeptide GFLG (0.065 mmol) was dissolved in 0.9 ml DMF and, after cooling to −18° C., a solution of 13.5 mg of DCC (0.065 mmol) in 0.1 ml DMF was added. After 30 min, a solution of 10 mg of second-generation dendrimer BPA (0.052 mmol hydroxy groups) in 0.5 ml DMF was added to the cooled reaction mixture. The mixture was stirred for 90 min at 4° C. and at room temperature for another 2 h. Then the reaction mixture was diluted to 5 ml with methanol and the modified dendrimer was purified by removing low-molecular-weight impurities by gel chromatography on a column filled with Sephadex LH-20 in methanol (RI detection). The fractions containing dendrimers were concentrated on a rotary vacuum evaporator to 1 ml and the dendrimer was isolated by precipitation into diethyl ether. The free amino groups on modified dendrimer were obtained by deprotection of Fmoc-protected amino groups in a 25% solution of piperidine in DMF.

Example 14

Synthesis of Polymer Conjugates 1 and 2

Polymer conjugate 1 or 2 with a drug bound via amide bond to the end of oligopeptide sequence was prepared by the reaction of PDS groups of modified PAMAM or BPA dendrimer with thiol groups of polymers 2c or 2d.

150 mg of poly(HPMA-co-MA-GFLG-Dox)-AE-SH (0.010 mmol SH groups) was dissolved in 3 ml of 0.5 M phosphate buffer with 0.1 M NaCl and 0.01 M ethylenediaminetetraacetic acid (EDTA), pH 7.4) and the solution was added to a stirred solution of 6.5 mg of dendrimer-PDS (0.013 mmol PDS groups) in 1 ml methanol added to a stirred solution of dendrimer-PDS (0.013 mmol PDS groups) in 1 ml of methanol at laboratory temperature. After 4-h reaction at room temperature, the solution was diluted to 10 ml of methanol and the polymer conjugate was purified by removing low-molecular-weight impurities by gel chromatography on Sephadex LH-20 in methanol. The polymer fractions were concentrated on a rotary vacuum evaporator to 2 ml and the copolymer was isolated by precipitation into 30 ml of ethyl acetate. The product was dried to constant weight.

Polymer conjugate 1 or 2 with hydrazone-bound drug was prepared by the reaction of the PDS groups of dendrimer-PDS with SH groups of polymer 2a or 2b, subsequent deprotection of hydrazide groups with trifluoroacetic acid (TFA) and Dox binding in methanol under acetic acid catalysis.

200 mg of poly(HPMA-co-MA-AH-NHNH-Boc)-SPA-AE-SH (0.014 mmol SH groups) was dissolved in 4 ml of 0.5 M phosphate buffer (0.1 M NaCl, 0.01 M ethylenediaminetetraacetic acid (EDTA), pH 7.4) and the solution was added at room temperature to a stirred solution of 8.5 mg of dendrimer-PDS (0.017 mmol of PDS group) in 1.5 ml of methanol. After 4-h reaction at room temperature, the solution was diluted to 13 ml with methanol and the polymer carrier was purified by removing low-molecular-weight impurities by gel chromatography on a Sephadex LH-20 column in methanol. Polymer fractions were concentrated on a rotary vacuum evaporator to 2 ml and the copolymer was isolated by precipitation into 30 ml of ethyl acetate. The product was dried to constant weight. In deprotection of the Boc-protected polymer carrier, 190 mg of the carrier was dissolved in 5 ml of a TFA-triisopropylsilane-water 95:2.5:25 mixture. After 15 min, the mixture was repeatedly evaporated with methanol (five-fold excess) on an evaporator in water pump vacuum until small crystals precipitated. The product was dissolved in water and pH of its solution was adjusted to pH 7-8. The polymer carrier was purified by removing low-molecular-weight impurities by gel chromatography on a Sephadex G-25 column in distilled water (RI detection). The polymer was isolated from polymer fractions by lyophilisation in a Lyovac GT-2 device. For binding Dox, 180 mg of polymer carrier was dissolved in 2 ml of methanol and the solution was transferred into a thermostatted cell in which was 20 mg of Dox.HCl (0.034 mmol). The obtained nonhomogeneous suspension was stirred in the dark at 25° C. and, after 1 min, 100 µl of acetic acid was added. During the reaction, the suspension successively dissolved and, after 23-h reaction, the polymer product was purified by removing low-molecular-weight impurities and free drug by gel chromatography on a Sephadex LH-20 column in methanol. The polymer fractions were concentrated on a rotary vacuum evaporator to 3 ml. The polymer conjugate was isolated by precipitation into 30 ml of ethyl acetate. The product was dried to constant weight.

Example 15

Synthesis of Polymer Conjugates 3 and 4

Polymer conjugate 3 or 4 containing a drug bound through an amide group via an oligopeptide was prepared by the reaction of amino-modified PAMAM or BPA dendrimer-GFLG-NH$_2$ with TT or OSu groups of polymer 1e, 1f or 1g—or by the reaction of succinimidyl or carboxyl groups of polymer 1h, poly(HPMA-co-MA-GFLG-Dox)-SPA-GFLG-OSu, with amino or hydroxy groups of the dendrimer.

100 mg of polymer if (0.006 mmol OSu groups) was dissolved in 2 ml DMSO and the solution was added at laboratory temperature to a stirred solution of 1.9 mg of dendrimer (0.009 mmol GFLG-NH$_2$ groups) in 1 ml of methanol. After 2-h reaction at laboratory temperature, the solution was diluted to 8 ml with methanol and the polymer conjugate was purified by removing low-molecular-weight impurities by gel chromatography on a Sephadex LH-20 column in methanol. Polymer fractions were concentrated on a rotary vacuum evaporator to 2 ml and the copolymer conjugate was isolated by precipitation into 30 ml of ethyl acetate. The product was dried to constant weight.

Polymer conjugate 3 or 4 with a hydrazone-bound drug was prepared by the reaction of amino groups of modified PAMAM or BPA dendrimer-GFLG-NH$_2$ with TT or OSu groups of polymers 1a, 1b or 1c, or by the reaction of succinimidyl groups or in some cases of carboxyl groups of polymer 1d poly(HPMA-co-MA-AH-NHNH-Boc)-SPA-GFLG-OSu with amino or hydroxy groups of a dendrimer, subsequent deprotection of hydrazide groups with trifluoroacetic acid (TFA) and attaching Dox in methanol under acetic acid catalysis.

120 mg of poly(HPMA:co-MA-AH-NHNH-Boc)-GFLG-OSu (0.008 mmol OSu groups) was dissolved in 2 ml DMSO and the solution was added at laboratory temperature to a stirred solution of 2.2 mg of a dendrimer (0.011 mmol NH$_2$ groups) in 1 ml of methanol. After 2-h reaction at laboratory temperature, the solution was diluted to 9 ml with methanol and the polymer carrier was purified by removing low-molecular-weight impurities by gel chromatography on a Sephadex LH-20 column in methanol. Polymer fractions were concentrated on a rotary vacuum evaporator to 2 ml and the copolymer carrier was isolated by precipitation into 30 ml of ethyl acetate. The product was dried to constant weight.

The removal of Boc protecting groups and attachment of a drug with the hydrazone bond were carried out by the procedure described in Example 14.

Example 16

Release of Doxorubicin from Polymer Conjugates

Figure 2:
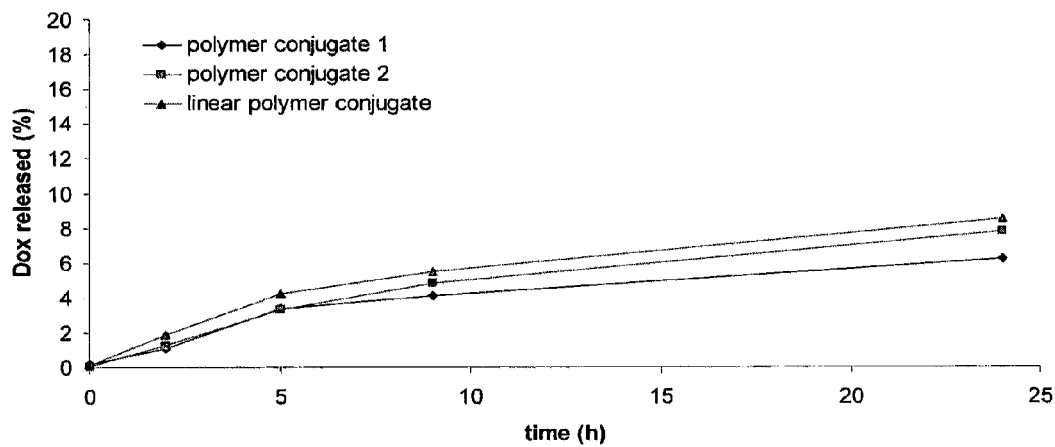
FIG. 2 shows the time dependence of the Dox released from dendritic polymer conjugates 1 and 2, and the linear polymer conjugate 3 at pH 7.4. (Dox is bound through hydrazone bonds) incubated in a buffer of pH 7.4 (modelling bloodstream).

The amount of doxorubicin released from polymer conjugates was measured after their incubation in 0.1 M phosphate buffer of pH 5.0 (0.05 M NaCl) modelling intracellular medium and in phosphate buffer of pH 7.4 modelling the bloodstream medium. The released Dox in the incubation solution was determined by HPLC (Shimadzu). In the predetermined time intervals, 50-µl samples of the solution were withdrawn and analyzed on a TSKGel G 3000×1 column, with isocratic flow rate 0.5 ml/min of the mobile phase consisting of a methanol-acetate (80:20 vol.%) buffer of pH 6.5. The Dox amount was calculated from the peak areas of free and bound Dox (UV-VIS detection at 488 nm). After incubation of conjugate solutions (of concentrations 5 mg/ml) in a physiological medium at 37° C. (phosphate buffer, pH 7.4), only a small amount of the drug is released (up to 7%/24 h, FIG. 2). In contrast, the rate of Dox release from polymer conjugates and hence the rate of activation of a cytotoxic drug in a mildly acid medium at pH 5.0 is considerable (FIG. 1). The release rates from graft polymer conjugates at pH 7.4 and pH 5 are fully comparable with those found with the hydrazone conjugates prepared from linear or graft copolymers [Etrych 2008].

Example 17

Degradation of Polymer Conjugate I with Amide Bond-Bound Drug Using Glutathione to Degradation Products which Can Be Eliminated from the Organism Degradation of polymer conjugates was studied in 0.1 M phosphate buffer (0.05 M NaCl, pH 6) in the presence of glutathione as reducing agent, i.e. in the medium modelling the cell (cytoplasm, endosome and secondary lysosome). Polymer conjugates were dissolved in phosphate buffer at a concentration of 20 mg/ml. Immediately before placing the solutions in a thermostat (37° C.), a glutathione stock solution was added so that the resulting glutathione concentration in the incubation medium was $3.10^{-3}$ mol/l.

Aliquot samples (200 µl) of incubation solutions were withdrawn in predetermined time intervals, desalted on PD-10 columns and lyophilized. Molecular weights of degradation products were measured on a liquid chromatograph Shimadzu LC-10AD equipped with a refractometer (Optilab Rex, Wyatt Technology, USA) and multiangle light-scattering detector (DAWN EOS, Wyatt Technology, USA). The analysis was performed on a Superose™ 6 column (300×10 mm; Amersham Bioscience). As mobile phase, 0.3 M acetate buffer (pH 6.5, 0.5 g/l NaN$_3$) with a flow rate of 0.5 ml/min was used. Molecular weight and polydispersity of the copolymer was calculated using Astra software (Wyatt Technology, USA).

Figure 3:
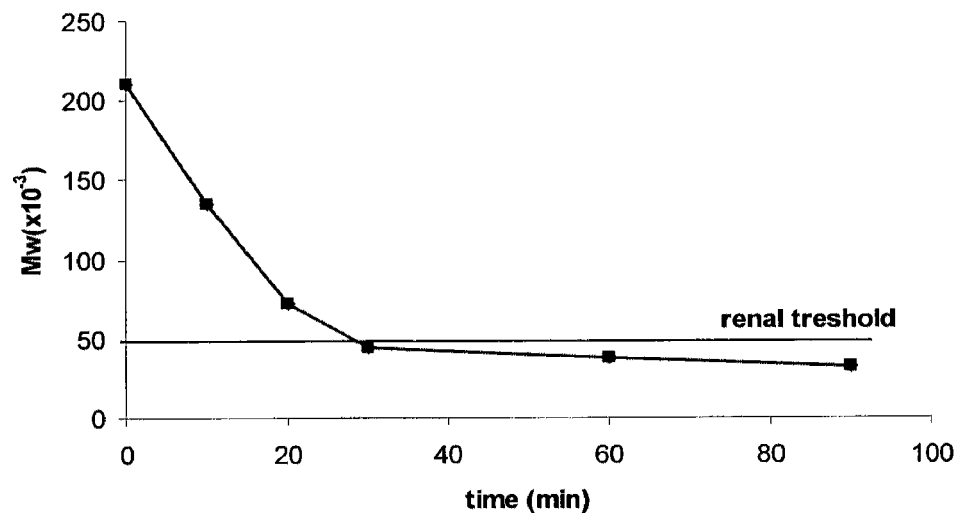
FIG. 3 shows the time dependence of the molecular weight of polymer conjugate 1 incubated in phosphate buffer containing glutathione ($c = 3.10^{-3}$ mol/l).

The conjugate with disulfide bridges (conjugate I) in a solution containing cytoplasmatic concentration of glutathione ($3.10^{-3}$ mol/l) rapidly degrades. After 24-h incubation with glutathione, polymer degradation products with molecular weights below the renal filtration limit (~25000 g/mol) were found (FIG. 3).

Example 18

Figure 4:
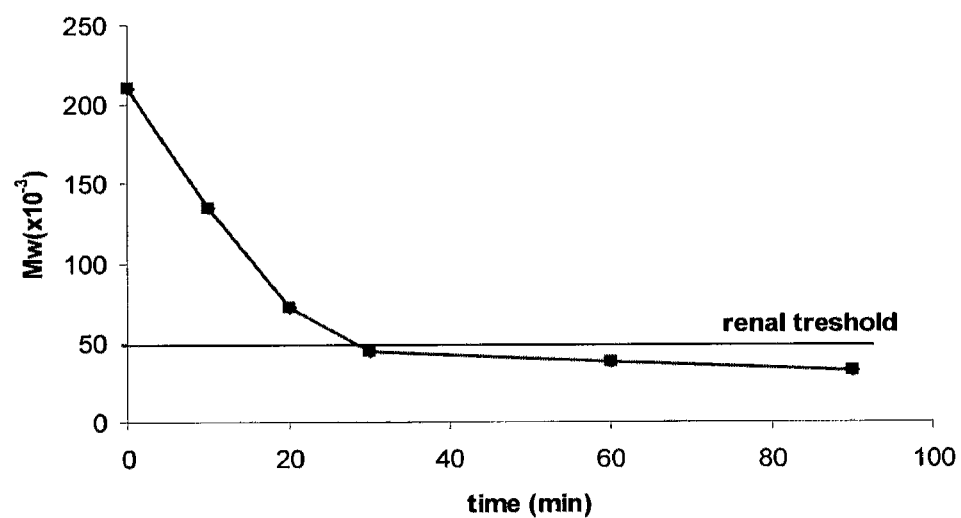
FIG. 4 shows the time dependence of the molecular weight of polymer conjugate 3 during incubation in phosphate buffer containing cathepsin B ($c = 5.1^{-7}$ mol/l).

Degradation by Cathepsin B of Polymer Conjugate 3 with Hydrazone Bond-Bound Drug to Degradation Products, Which Can Be Eliminated From The Organism Degradation of polymer conjugate was studied in 0.1 M phosphate buffer (NaH$_2$PO$_4$/NaOH, pH 6.0, 5 mM glutathione, 1 mM EDTA) containing lysosomal enzyme cathepsin B, thus modelling the medium of secondary lysosome in tumor cells at a substrate concentration of 50 mg/ml. The polymer conjugate was dissolved in phosphate buffer at concentration 10 mg/ml and, immediately before placement in a thermostat (at 37° C.), a stock solution of cathepsin B was added so that its resulting concentration was $5.10^{-7}$ M. Samples (200 µl) of incubation solutions were withdrawn in predetermined time intervals, desalted on a PD-10 column and lyophilized. Molecular weights of degradation products were measured in the same way as described above. The conjugate containing a GFLG oligopeptide spacer (conjugate 3) slowly degraded in a solution of cathepsin B ($5.10^{-7}$ mol/l). After 48-h incubation with cathepsin B, polymer degradation products with molecular weights below the renal filtration limit (~40000 g/mol) were found (FIG. 4).

For examples of biological activity, the following codes for polymer conjugates are defined:
K-1 AM—dendritic polymer conjugate 1 with amide bond-bound drug, M$_w$=248,000, I$_n$=1.9, R$_h$=15.6 nm.
K-1 HYD—dendritic polymer conjugate 1 with hydrazone bond-bound drug, M$_w$=199,000, I$_n$=2.1, R$_h$=14.2 nm
LIN AM—linear polymer conjugate with amide bond-bound drug, M$_w$=45,000, I$_n$=1.85, R$_h$=5.2 nm.
LIN HYD—linear polymer conjugate with hydrazone bond-bound drug, M$_w$=36,000, I$_n$=1.87, R$_h$=4.5 nm.

Example 19

Example of in vitro biological activity (cytotoxicity, IC$_{50}$), of dendritic and graft conjugates of doxorubicin incubated with cells of various tumor lines (the method of [$^3$H]thymidine incorporation was used)

TABLE 1

Cytotoxicity, IC$_{50}$) of dendritic and graft conjugates of doxorubicin incubated with cells of various tumor lines

| Tumor line | K-1 HYD | K-1 AM | LIN HYD | LIN AM | Dox |
| --- | --- | --- | --- | --- | --- |
| EL4 | 0.059 | 11.886 | 0.147 | 24.1 | 0.014 |
| 38C13 | 0.015 | 2.000 | 0.023 | 1.796 | 0.003 |
| B16 | 0.012 | 1.120 | 0.030 | 1.562 | 0.005 |
| BCL 1 | 0.003 | 0.700 | 0.042 | 0.945 | 0.001 |
| Raji | 0.005 | 1.272 | 0.028 | 2.71 | 0.001 |
| Jurkat | 0.016 | 3.476 | 0.599 | 4.83 | 0.003 |
| 3T3 | 0.015 | 2.751 | 0.0269 | 2.974 | 0.005 |
| FaDu | 0.038 | 1.873 | 0.032 | 6.22 | 0.001 |
| 4T1 | 0.053 | 3.657 | 0.191 | 19.43 | 0.012 |

To determine the inhibition activity of the studied polymers, the following permanent tumor lines of mouse and human origin were selected: mouse T cell lymphoma EL4, mouse B cell lymphoma 38C13, mouse melanoma B16, mouse B cell leukemia BCL1, human B cell lymphoma Raji, human T cell leukemia Jurkat, mouse fibroblastoma 3T3, human spinocellular carcinoma FaDu and mouse breast carcinoma 4T1. Antiproliferation activity was measured by incorporation of [$^3$H]thymidine.

It follows from Table 1 that the most pronounced inhibition activity in all the tested lines is shown with both the hydrazone bond-bound doxorubicin polymer conjugates (K-1 HYD a LIN HYD). The conjugates with amide bond-bound doxorubicin show a considerably lower activity. High-molecular-weight polymer conjugates K-1 HYD and K-1 AM show a slightly higher antiproliferation activity than the linear conjugates with the drug bound in the same way. The differences are not significant and it can be stated that the high-molecular-weight polymer conjtigates show approximately the same antiproliferation activity as their linear analogs with lower molecular weight.

Example 20

Example of In Vivo Biological Activity of Dendritic Polymer—Doxorubicin Conjugates in Inbred Mice C57BL/6 with Subcutaneously-Transplanted T-Cell Lymphoma EL4

For in vivo experiments, inbred mice C57BL/6 with subcutaneously transplanted T cell lymphoma EL4 were used. The doses were 1×15 mg Dox equivalent/kg and 10 mg Dox equivalent/kg, administered intravenously (i.v.). As an active control, a group of mice bearing EL4 tumor was used, which were treated with doxorubicin only (2×5 mg/kg i.v. on days 8 and 15). Basic control was untreated mice with EL4 tumor. Tumor growth after administering K-1 HYD with hydrazone-bound doxorubicin, K-1 AM with amide-bound doxorubicin and linear polymer conjugates LIN HYD and LIN AM is shown in FIG. 5.

Figure 5:
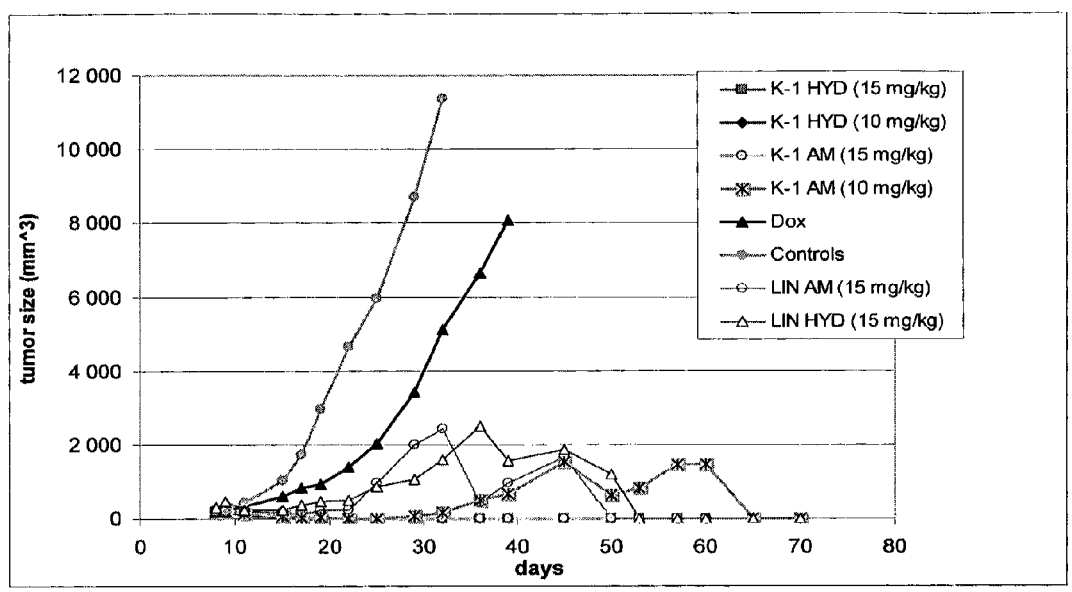
FIG. 5 represents the tumor growth after administration of K-1 HYD with hydrazone-bound doxorubicin, K-1 AM with amide bond-bound doxorubicin and linear polymer conjugates LIN HYD a LIN AM.
Figure 6:
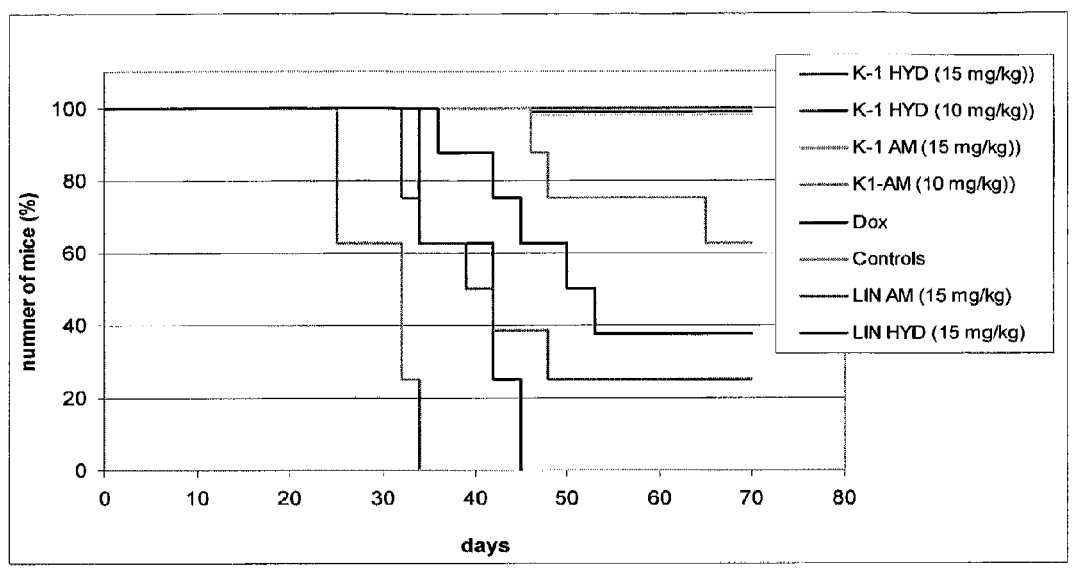
FIG. 6 show the survival of mice with EL4 tumor after administration of K-1 HYD with hydrazone bond-bound doxorubicin, K-1 AM with amide bond-bound doxorubicin and linear polymer conjugates LIN HYD a LIN AM.

It is evident from FIGS. 5 and 6 that both samples of dendritic HMW polymer conjugates (K-1 HYD a K-1 AM) in a dose of 15 mg Dox equivalent/kg are highly efficient. A single dose of the drug administered in the period of aggressive tumor growth is able to cure 100% of mice with experimental tumor EL4. The efficiency of HMW polymer conjugates is significantly higher than that of linear conjugates bearing the drug bound in a similar way. With these linear conjugates, 37% (LIN HYD) or 25% (LIN AM) of mice with experimental tumors were healed. At a dose of 10 mg Dox equivalent/kg, it was found that K-1 HYD with hydrazone bond-bound doxorubicin is always highly active, as a single dose administered in the period of aggressive tumor growth led again to healing of 100% of mice. Polymer conjugate K-1 AM with amide bond-bound doxorubicin is less active, but still a single low dose heals over 60% of mice with experimental tumor.

Figure 7:
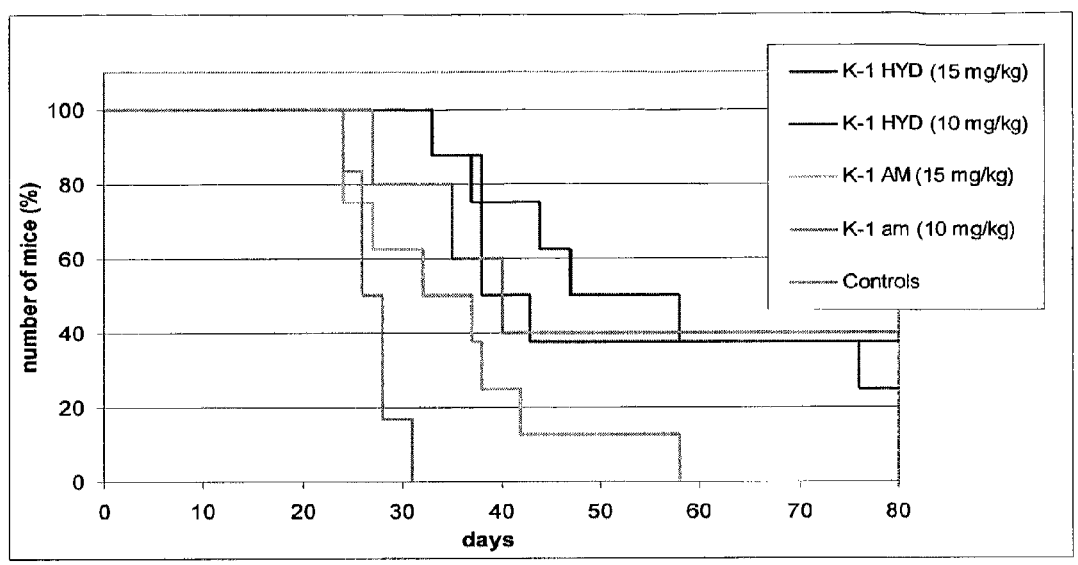
FIG. 7 represents the survival of mice cured with polymer conjugates (see FIGS. 5 and 6) and retransplanted with a lethal dose of the original tumor cells (mouse T-cell lymphoma EL 4, $1 \times 10^5$ cells)

FIG. 7 shows survival of mice healed with polymer conjugates (see FIGS. 5 and 6) and those retransplanted with a lethal dose of the original tumor (1×10$^5$ mouse T cell lymphoma EL4). The mice were not treated. It is evident from the results given in FIG. 7 that in mice treated with polymer conjugates, antitumor resistance developed during the treatment. This occurred with 30-40% of mice healed with K-1 HYD containing hydrazone-bound doxorubicin (doses 10 and 15 mg Dox equivalent/kg) and K-1 AM containing amide bond-bound doxorubicin (10 mg Dox equivalent/kg). This result means that the newly prepared polymer drugs according to the invention show two effects: a cytostatic effect, which directly kills a large majority of tumor cells and an immunomodulation effect, which stimulates the immunity system during the treatment and induces antitumor resistance. The results obtained after retransplantation of a lethal dose of tumor cells to the previously treated animals are experimental evidence of the fact that the therapy with polymer conjugates according to the invention leads not only to elimination of tumor, but also protects the healed animals against secondary/metastatic evolution of cancer or its recurrence.

REFERENCES

Bae, Y. S.; Fukushima, S.; Harada, A.; Kataoka, K. pH responsive drug-loaded polymeric micelles: Intracellular drug release correlated with in vitro cytotoxicity on human small cell lung cancer SBC-3. *Winter Symposium and 11th International Symposium on Recent Advances in Drug Delivery Systems*. Salt Lake City, Utah, U.S.A. 2003. Salt Lake City, Utah, U.S.A.

Bai S., Ahsan F., Synthesis and Evaluation of Pegylated Dendrimeric Nanocarrier for Pulmonary Delivery of Low Molecular Weight Heparin, PHARMACEUTICAL RESEARCH *Pharm. Res.* 26, 539-548 (2009)

Bronich, T. K.; Nehls, A.; Eisenberg, A.; Kabanov, V. A.; Kabanov, A. V. *Colloids Surf B* 16, 243-251 (1999).

Chan, W. C.; White, P. D., Eds., *"Fmoc Solid Phase Peptide Synthesis: A Practical Approach"*, Oxford University Press, Oxford 2000.

Duncan, R., Lloyd, J. B., J. Kopeček, P. Rejmanová, J. Strohalm, K. Ulbrich, B. Říhová, V. Chytrý: Synthetic Polymeric Drugs (1985). Patent CZ 0095/85, Australia 589587, Canada 130053, Denmark 164485, Europe 0187547, US 5,037,883, Japan 000137/86

Etrych T., Chytil P., Ulbrich K., Říhová B, Polymerní léčivo a způsob jeho výroby (Grafted Macromolecular conjugates of doxorubicin with anticancer activity and method of their preparation), Patent CZ 298 945 B6

Etrych T., Chytil P., Mrkvan T., Šírová M., Říhová B., Ulbrich K., Conjugates of doxorubicin with graft HPMA copolymers for passive tumor targeting, *J. Controlled Release* 132, 184-192 (2008)

Chytil P., Etrych T., Hrubý, M., Ulbrich K., Říhová B., Micelární nosiče doxorubicinu s protinádorovou aktivitou, Patent Application CZ 2006-207

Gajbhiye V., Kumar P., Tekade R., Jain N., PEGylated PPI dendritic architectures for sustained delivery of H-2 receptor antagonist, *Eur. J. Med. Chem.* 44, 1155-1166 (2009)

Kataoka, K.; Harada, A.; Nagasaki, Y. *Adv. Drug Delivery Rev.* 47, 113-131 (2001).

Kopeček, J., Kopečková, P., Minko, T., Lu, Z. R., Peterson, C. M.; "Water soluble polymers in tumor targeted delivery". *J. Controlled Release* 74, 165-173 (2001).

F. Kratz, U. Beyer, M. T. Schutte, Drug-polymer conjugates containing acid-cleavable bonds, *Crit. Rev. Ther. Drug Carrier Syst.* 16, 245-288 (1999).

Lele, B., Leroux, J.,: Amphiphilic diblock, triblock and star-block copolymers and their pharmaceutical compositions, Patent U.S. Pat. No. 7,018,655

Maeda, H., J. Wu, T. Sawa, Y. Matsumura, and K. Hori, Tumor vascular permeability and the EPR effect in macromolecular therapeutics: a review. *J Controlled Release* 65:271-284 (2000).

Li, Ch., Vega, J., Wallace, S., Tansey, W., Charnsangavej, Ch.: DENDRITIC POLY (AMINO ACID) CARRIERS AND METHODS OF USE, Patent WO 03055935

T. Mrkvan, M. Šírová, T. Etrych, P. Chytil, J. Strohalm, D. Plocová, K. Ulbrich, B. Říhová, Chemotherapy based on HPMA copolymer conjugates with pH-controlled release of doxorubicin triggers anti-tumor imunity, J. Controlled Release 110, 119-129 (2005).

Y. Noguchi, J. Wu, R. Duncan, J. Strohalm, K. Ulbrich, T. Akaike, H. Maeda, *Jpn. J. Cancer Res.* 89, 307-314 (1998)

P. Rejmanová, J. Labský, J. Kopeček, Aminolyses of Monomeric and Polymeric 4-nitrophenyl Esters of N-Methacroylamino Acids, *Makromol. Chem.* 178, 2159-2168 (1977)

F. Rypáček, J. Drobnik, V. Chmelat, J. Kalal, The renal excretion and retention of ??macromolecules—the chemical structure effect, *Pflug. Arch. Eur. J. Pgy.* 392, 211-217 (1982)

B. Říhová, M. Jelínková, J. Strohalm, V. Šubr, D. Plocová, O. Hovorka, M. Novák, D. Plundrová, Y. Germano, K. Ulbrich, Polymeric Drugs Based on Conjugates of Synthetic and Natural Macromolecules II. Anti-cancer Activity of antibody or (Fab')$_2$-targeted Conjugates and Combined Therapy with Immunomodulators. *J. Controlled Release.* 64, 241-261 (2000)

L. W. Seymour, Y. Miyamoto, H. Maeda, M. Brereton, J. Strohalm, K. Ulbrich, R. Duncan, *Eur. J. Cancer A* 31, 766-770 (1995)

V. Šubr, K. Ulbrich, B. Říhová, Reactive polymers and copolymers based on N-(2-hydroxypropyl) methacrylamide, a method of their preparation and their use for synthesis of polymer drugs, for modification of biologically active proteins and for gene transport systems, Patent Application CZ PV 2003-1950

V. Šubr, Č. Koňák, R. Laga, K. Ulbrich, Coating of DNA/poly(L-lysine) complexes by covalent attachment of poly[N-(2-hydroxypropyl)methacrylamide], *Biomacromolecules* 7, 122-130 (2006)

K. Ulbrich, V. Šubr, J. Strohalm, D. Plocová, M. Jelinková, B. Říhová, Polymeric Drugs Based on Conjugates of Synthetic and Natural Macromolecules I. Synthesis and Physicochemical Characterisation. *J. Controlled Release* 64, 63-79 (2000)

K. Ulbrich, T. Etrych, P. Chytil, M. Jelínková, B. Říhová, Antibody-Targeted Polymer-Doxorubicin Conjugates with pH-Controlled Activation, *J. Drug Targeting* 12, 477-489 (2004)(A).

K. Ulbrich, V. Šubr, Polymeric Anticancer Drugs with pH-Controlled Activation, *Adv. Drug Delivery Rev.* 56/7, 1025-1052 (2004) (B)

D. Wang, P. Kopeckbva, T. Minko, V. Nanayakkara, J. Kopecek, Synthesis of Star-Like N-(2-Hydroxypropyl)methacrylamide Copolymers—Potential Drug Carriers, *Biomacromolecules* 1, 313-319 (2000).

The invention claimed is:

1. A dendritic high-molecular-weight polymer drug carrier characterized in that it consists of a central dendritic part of zero to sixth generation of dendrimer selected from the group consisting of amidoamine- and 2,2-bis(hydroxymethyl)propanoic units, the amino or hydroxy end groups of which are grafted with semitelechelic copolymers of N-(2-hydroxypropyl) methacrylamide (HPMA) through amide or ester bond and biodegradable spacers.

2. The polymer drug carrier according to claim 1 characterized in that it consists of a central amidoamine dendrimer, the amino groups of which are grafted with a semitelechelic HPMA copolymer attached to the dendrimer with the ends of polymer chains via amide bond and a biodegradable spacer formed by disulfide bond, as shown in structure I or a biodegradable spacer formed by a oligopeptide sequence SP2 as shown in structure II

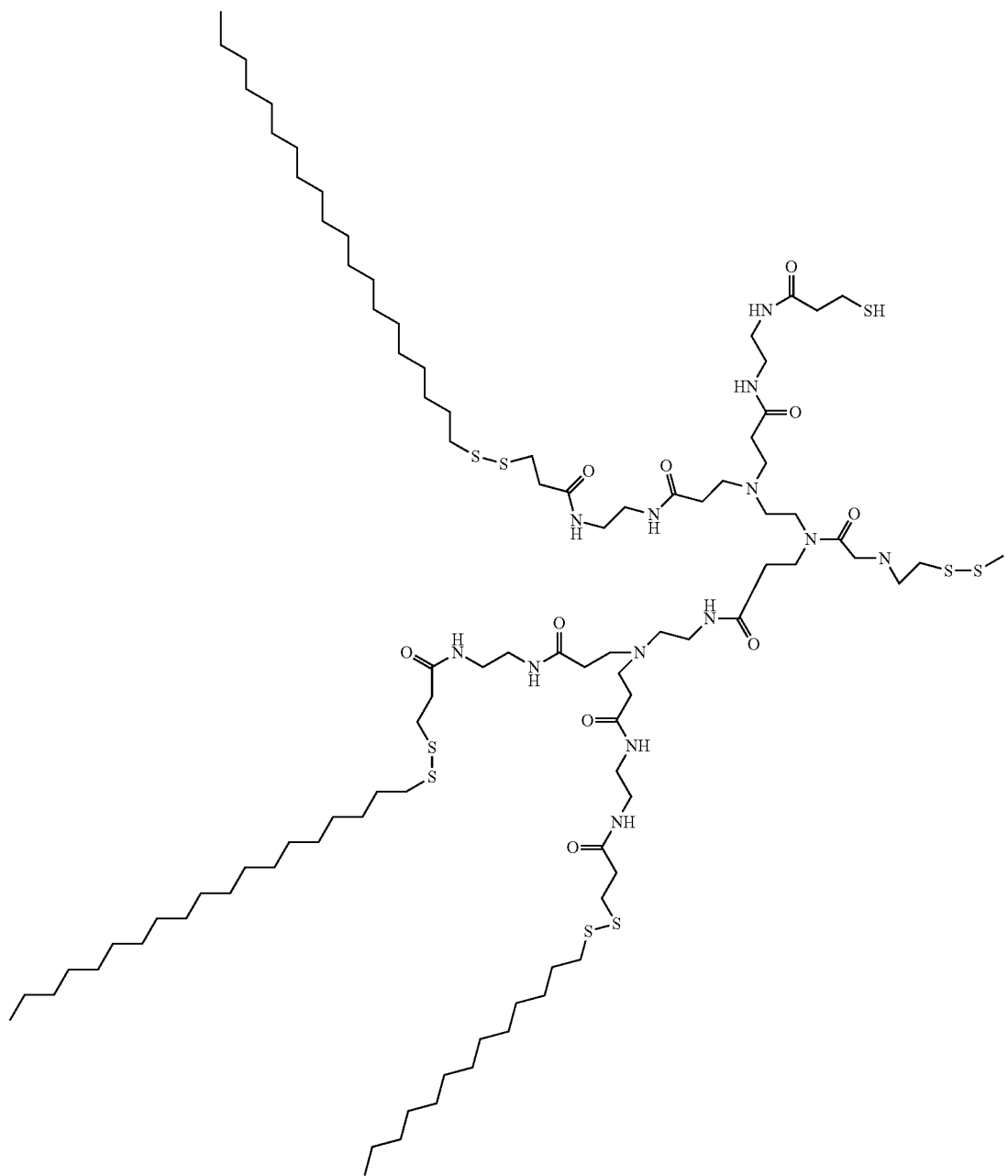
I

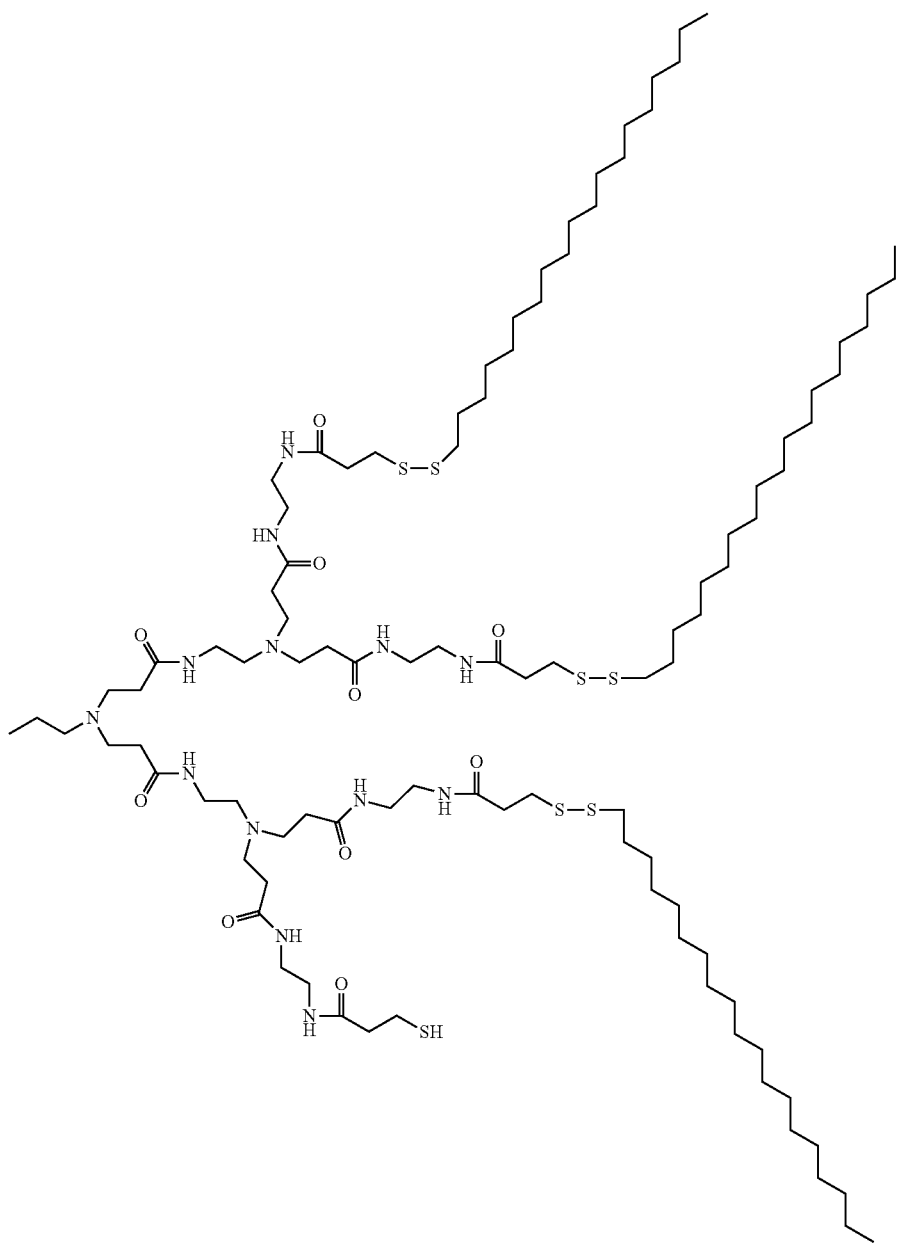 [SMILES: CCCCCCCCCCCCCCCCCCCSSCCC(=O)NCCNC(=O)CCN(CCNC(=O)CCN(CCC)CCC(=O)NCCN(CCC(=O)NCCNC(=O)CCSSCCCCCCCCCCCCCCCCCCC)CCC(=O)NCCNC(=O)CCSSCCCCCCCCCCCCCCCCCCC)CCC(=O)NCCNC(=O)CCS]

-continued
II
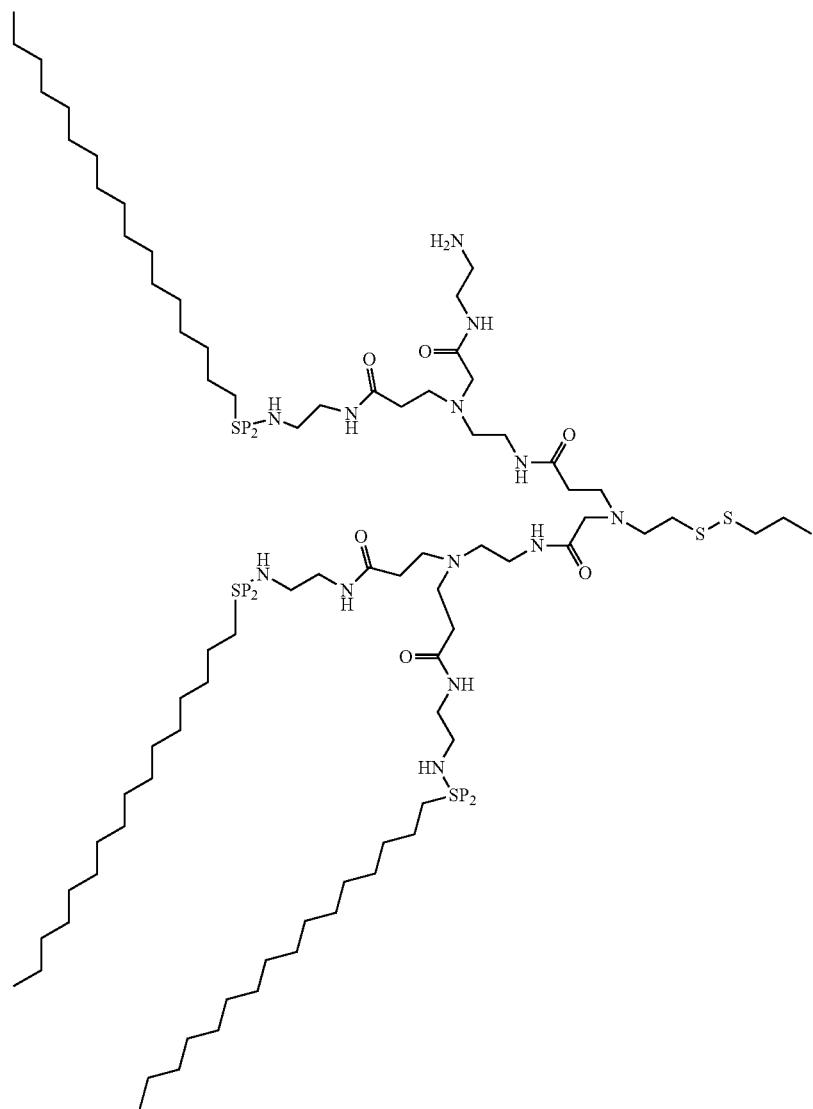

-continued

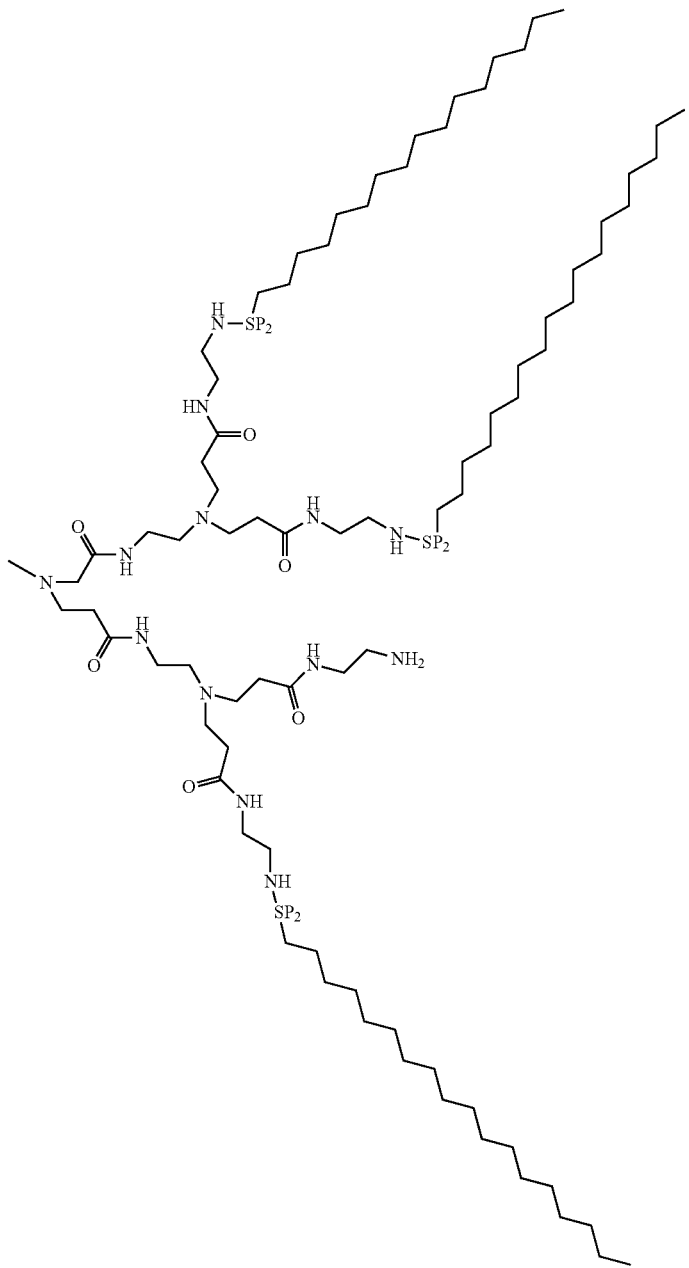

wherein zig-zag lines in structure I and In structure II represent HPMA chains.

3. Polymer carrier according to claim 1, characterized in that it consists of a central dendrimer based on 2,2-bis(hydroxymethyl)propanoic acid, the hydroxy groups of which are grafted with semitelechelic HPMA copolymer chains attached in turn to the dendrimer by the chain-end ester bond and a biodegradable spacer containing disulfide bond as shown in structure III or by means of oligopeptide sequence SP2 as shown in structure IV

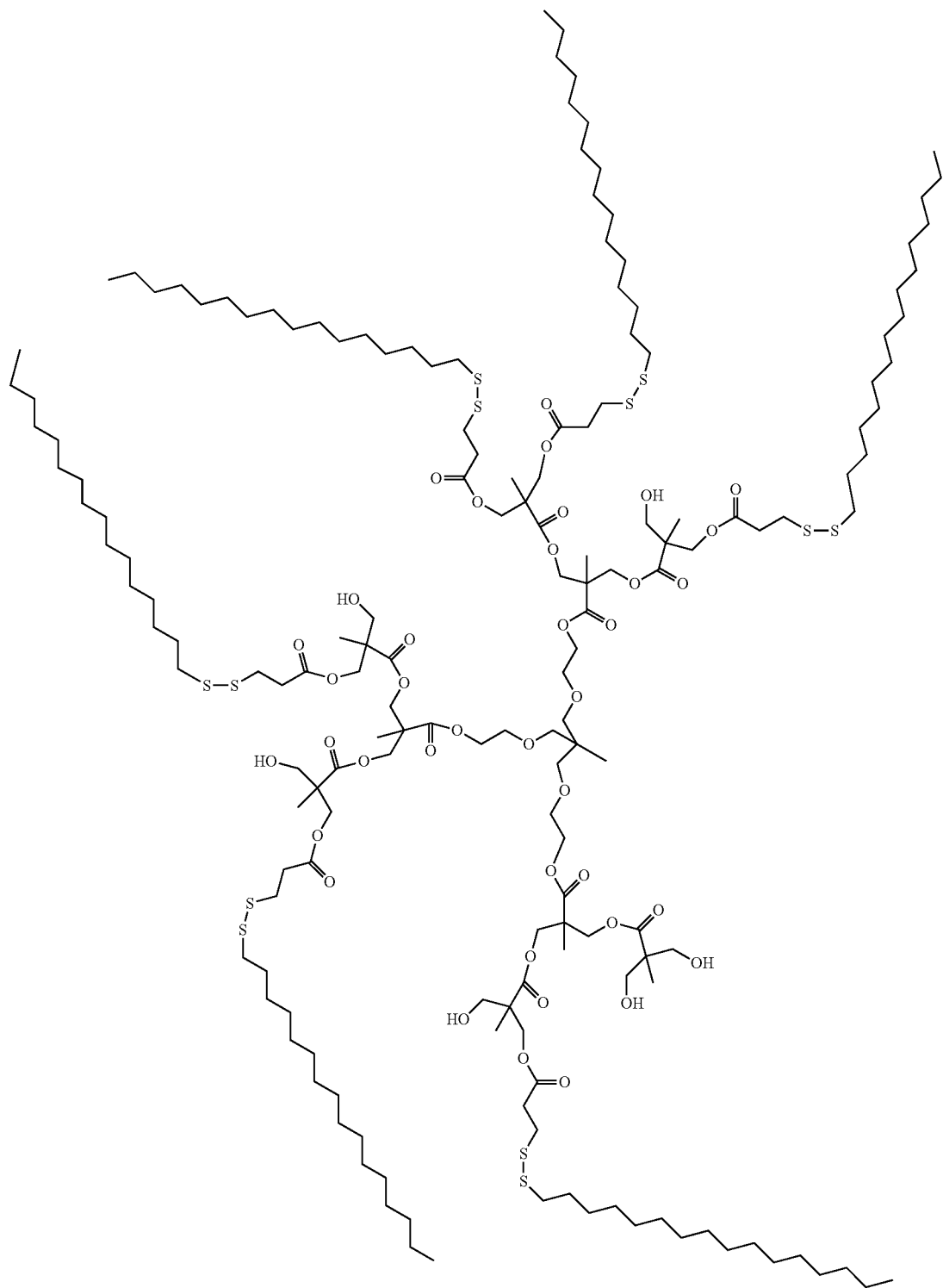

-continued
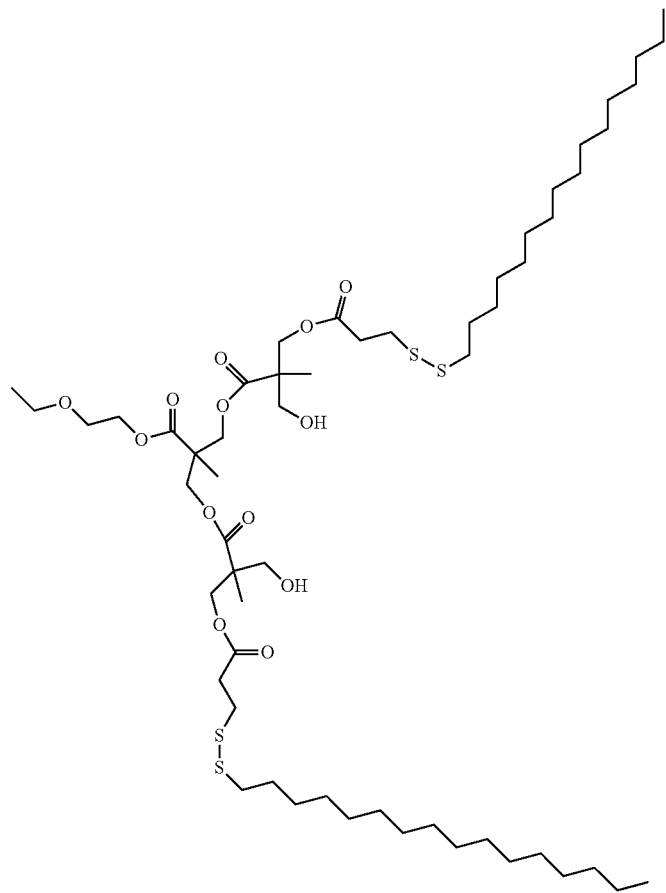 [SMILES: CCCCCCCCCCCCCCCCSSCCC(=O)OCC(C)(CO)C(=O)OCC(C)(COC(=O)C(C)(CO)COC(=O)CCSSCCCCCCCCCCCCCCCC)C(=O)OCCOCC]

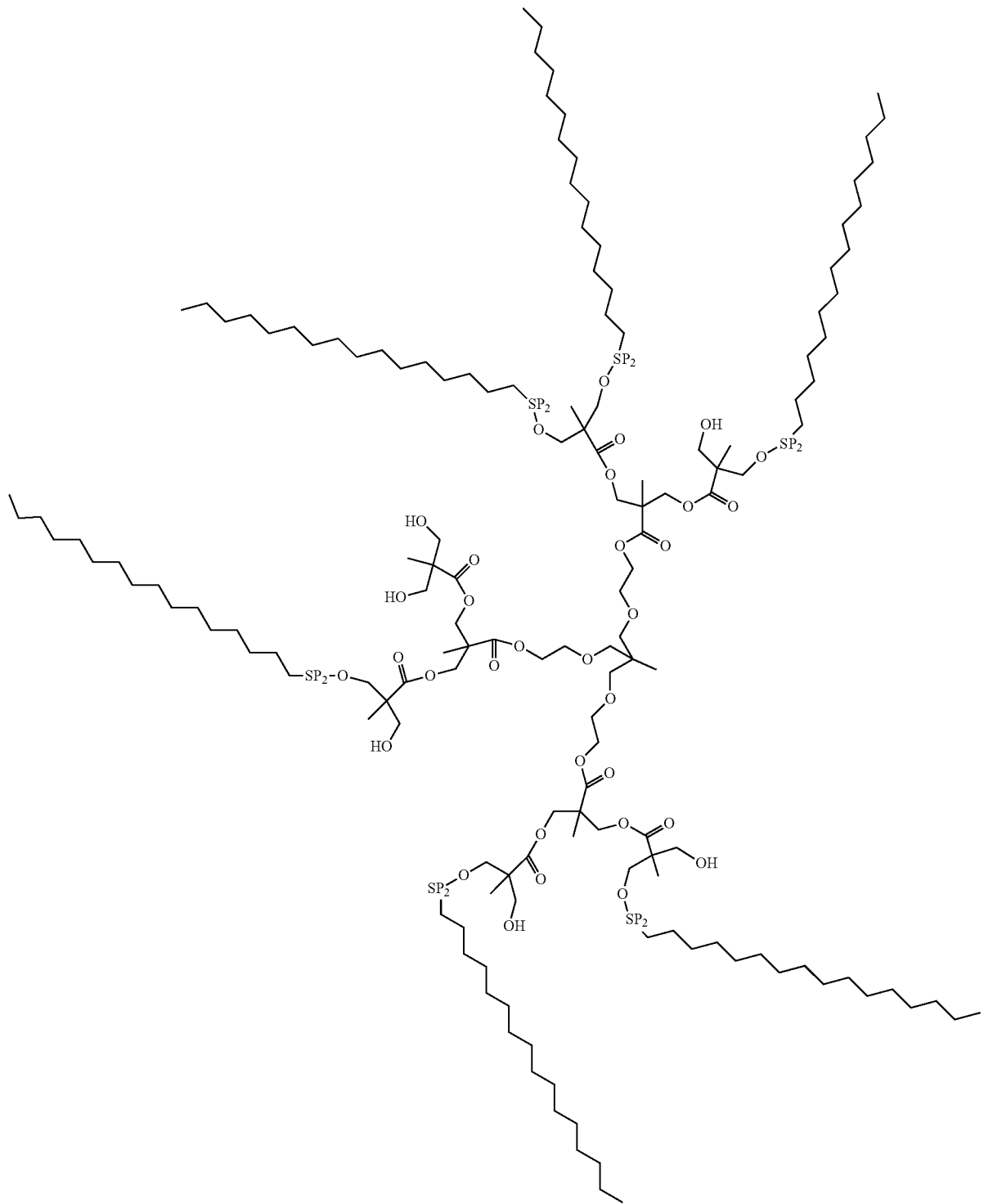
IV

-continued

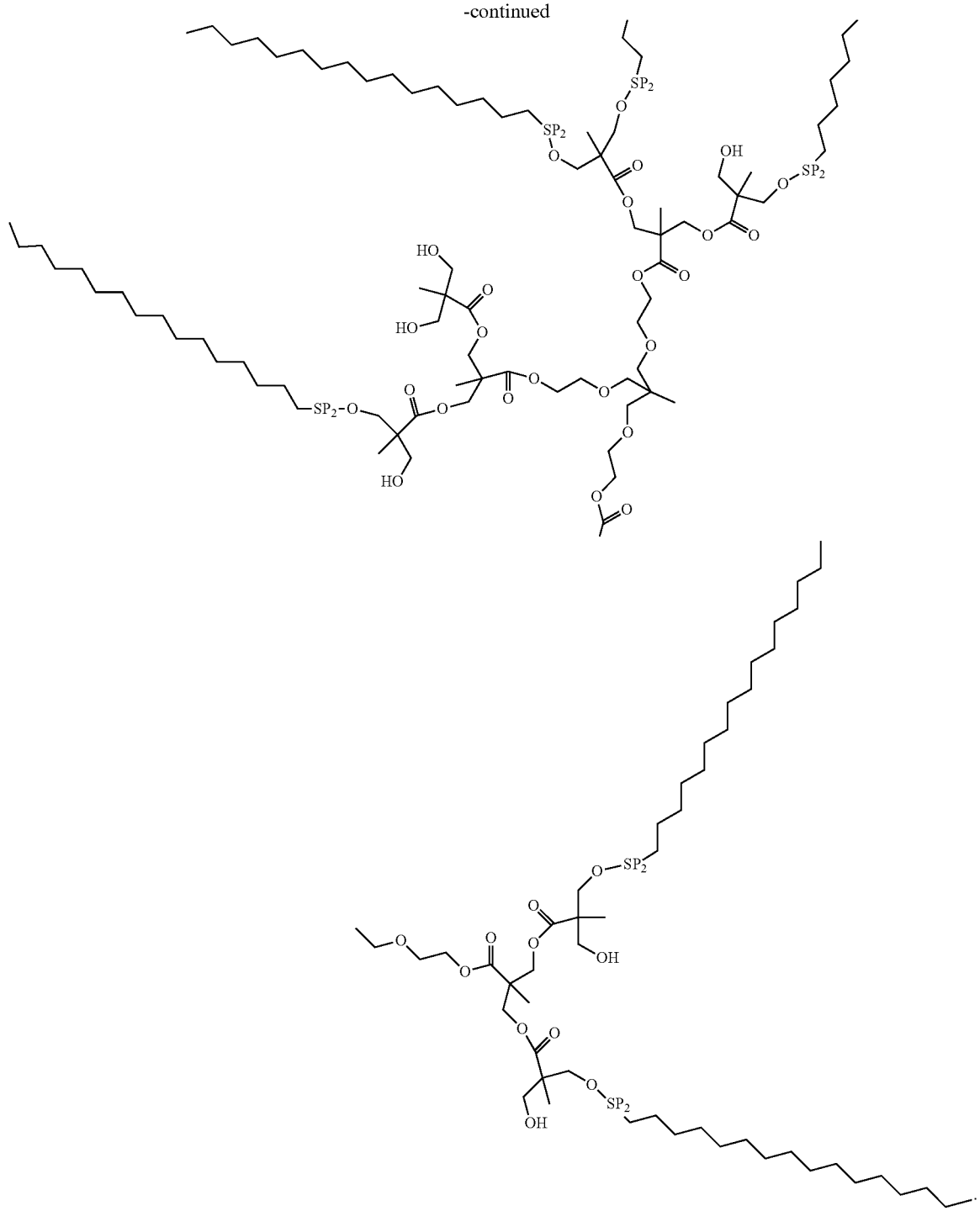

wherein zig-zag lines in structure III and in structure IV represent HPMA chains.

4. Polymer carrier according to claim 1, characterized in that its central part is formed by an amidoamine dendrimer of zero to sixth generation, containing 4-256 end groups selected from the group consisting of amino, pyridyldisulfanyl and carboxyl groups, with the core unit formed preferably by cysteamine, ethylenediamine, butane-1,4-diamine, hexane-1,6-diamine or dodecane-1,12-diamine.

5. Polymer carrier according to claim 1, characterized in that its central part is formed by a 2,2-bis(hydroxymethyl) propanoic dendrimer of zero to sixth generation, containing 8-256 end groups selected from the group comprising hydroxy, pyridyldisulfanyl and carboxyl group.

6. Polymer carrier according to claim 1 characterized in that 2-28 grafts are formed by HPMA copolymer containing 0.5-8 mol % of monomer units of methacryloylated hydrazide of aminoacyl SP1, where the aminoacyl is preferably selected from the group of glycyl, β-alanyl, 6-aminohexanoyl (AH), 4-aminobenzoyl and/or a combined acyl derived from oligopeptides GlyGly, GlyPheGly, GlyLeuGly, GlyLeuPheGly and GlyPheLeuGly.

7. Polymer carrier according to claim 1 characterized in that the polymer grafts are attached to central amidoamine or 2,2-bis(hydroxymethyl)propanoic dendritic by biodegradable spacer containing a disulfide group or a biodegradable oligopeptide SP2.

8. Polymer carrier according to claim 7 characterized in that the oligopeptide SP2 is selected preferably from the group of oligopeptides including GlyLeuGly, GlyPheGly, GlyPheLeuGly and GlyLeuPheGly.

9. Polymer conjugate characterized in that it consists of a polymer carrier according to claim 1 and a covalently bound drug.

10. Polymer conjugate according to claim 9, characterized in that it consists of a polymer carrier and a cancerostatic.

11. Polymer conjugate according to claim 10, characterized in that doxorubicin is attached to the carrier by a hydrolytically cleavable hydrazone bond.

12. Polymer conjugate according to claim 10, characterized in that it consists of a polymer carrier and an amide bond-bound drug, in which 2-28 polymer grafts are formed by a HPMA copolymer containing 0.5-8 mol % of monomer units of methacryloylated oligopeptide SP2 with doxorubicin attached to the end of oligopeptide through an amide bond, where the oligopeptide is preferably selected from the group consisting of oligopeptides GlyPheGly, GlyLeuGly, GlyLeuPheGly and GlyPheLeuGly.

13. Polymer conjugate according to claim 9, characterized in that the molecular weight of such dendritic system ranges preferably from 40,000 to 1,400,000 g/mol and the doxorubicin content, both in polymer chains and in the resulting dendritic conjugate ranges between 1 and 25 wt %.

14. A pharmaceutical composition containing as an active component a substance according to any of claim 9 for use in treatment of tumors.

15. A pharmaceutical composition according to claim 14, for use in treatment of solid tumors.

16. A pharmaceutical composition according to claim 14, for use in treatment of lymphomas and leukemias.

* * * * *